United States Patent [19]
Chen et al.

[11] Patent Number: 5,445,608
[45] Date of Patent: Aug. 29, 1995

[54] METHOD AND APPARATUS FOR PROVIDING LIGHT-ACTIVATED THERAPY

[75] Inventors: James C. Chen, 2011-87th Pl. N.E., Bellevue, Wash. 98004; Elric W. Saaski, Bothell, Wash.

[73] Assignee: James C. Chen, Bellevue, Wash.

[21] Appl. No.: 107,276

[22] Filed: Aug. 16, 1993

[51] Int. Cl.⁶ .............................................. A61N 1/30
[52] U.S. Cl. ...................................... 604/20; 604/19; 604/21
[58] Field of Search ............... 604/19, 20, 21

[56] References Cited

U.S. PATENT DOCUMENTS

| | | | |
|---|---|---|---|
| 4,558,690 | 12/1985 | Joyce | 604/20 |
| 4,822,335 | 4/1989 | Kawai et al. | 604/20 |
| 4,886,831 | 12/1989 | Morcos et al. | 604/20 |
| 4,932,934 | 6/1990 | Dougherty et al. | 604/20 |
| 4,957,481 | 9/1990 | Gatenby | 604/20 |
| 5,132,101 | 7/1992 | Vogel et al. | 604/20 |
| 5,146,917 | 9/1992 | Wagnières et al. | 604/21 |
| 5,163,898 | 11/1992 | Morcos et al. | 604/20 |
| 5,298,018 | 3/1994 | Narciso, Jr. | 604/21 |

OTHER PUBLICATIONS

Noguchi, H., "The Photodynamic Action of Eosin and Erythrosin upon Snake Venom," *J. of Exp. Med.*, 1906, vol. 8, pp. 252–266.
Bolande et al., "Photodynamic Action," *Anch. Path.*, 1963, vol. 75, pp. 115–122.
Ballio et al., "Research Progress in Organic-Biological and Medicinal Chemistry," ©*Societa Editoriale Farmaceutica*, 1964, vol. I, pp. 260–336.
Tapper et al., "Photosensitivity from Chlorophyll-Derived Pigments," *J. Sci. Fd Agric.*, 1975, vol. 26, pp. 277–284.
Ison et al., "Phototoxicity of Quinoline Methanols and Other Drugs in Mice and Yeast," *The Journal of Investigative Dermatology*, 1969, vol. 52, No. 2, pp. 193–198.
Eskins et al., "Sensitized Photodegradation of Cellulose and Cellulosic Wastes," *Photochemistry and Photobiology*, 1973, vol. 18, pp. 195–200.
Krinsky, N., "Cellular Damage Initiated by Visible Light," *Symposia of Society for General Microbiology*, 1976, pp. 209–239.
Song et al., "Photochemistry and Photobiology of Psoralens," *Photochemistry and Photobiology*, 1979, vol. 29, pp. 1177–1197.
Haas et al., "Photodynamic Effects of Dyes on Bacteria," *Mutation Research*, 1979, vol. 60, pp. 1–11.
Webb et al., "Photodynamic Effects of Dyes on Bacteria," *Mutation Research*, 1979, vol. 59, pp. 1–13.
Barltrop et al., "Potential Management of Florida Red Tide Through Selective Photodynamic Action," *J. Environ. Sci. Health*, 1980, A15(2), pp. 163–171.

(List continued on next page.)

*Primary Examiner*—C. Fred Rosenbaum
*Assistant Examiner*—N. Kent Gring
*Attorney, Agent, or Firm*—Ronald M. Anderson

[57] ABSTRACT

Light developed by an implantable probe is used to illuminate a treatment site that has been perfused with a photoreactive agent. A number of different embodiments of implantable probes are disclosed. Preferably, an array of light emitting diodes (LEDs) or solid-state laser diodes (LDs) are mounted on a light bar inside the implantable probe and are energized either using a storage battery power source, an inductively coupled external transformer, or with current provided in leads running through a flexible catheter that extends outside the patient's body to an external source. The implantable probe is normally intended to be disposed inside a patient's body during a surgical procedure, at a treatment site, and left in place for several days (or longer) after an incision is closed, while light produced by the array of LEDs or solid-state LDs irradiates the treatment site. Alternatively, light from an external light source can be conveyed over one or more optical fibers to an implantable probe that is disposed inside the patient's body to irradiate the treatment site. Waste heat produced by the array of LEDs or LDs disposed on the implantable probe can be employed to augment the PDT by increasing the temperature of the tissue at the treatment site.

61 Claims, 16 Drawing Sheets

OTHER PUBLICATIONS

Parris, J., "Photobiologic Considerations in Photoradiation Therapy," *Proceedings of a Porphyrin Photosensitization Workshop, Sep. 28–29, 1981, pp. 91–108.*

Bertoloni et al., "Photosensitizing Activity of Water- and Lipid-Soluble Phthalocyanines on *Escherichia coli,*" *FEMS Microbiology Letters* 71, 1990, pp. 149–156.

Gulliya et al., "Tumor Cell Specific Dark Cytotoxicity of Light-Exposed Merocyanine 540: Implications for Systematic Therapy Without Light," *Photochemistry and Photobiology,* 1990, vol. 52, No. 4, pp. 831–838.

Kennedy et al., "Photodynamic Therapy with Endogenous Protoporphyrin," *J. of Photochemsitry and Photobiology,* 1990, No. 6, pp. 143–148.

Gilliya et al., "Preactivation–A Novel Antitumour and Antiviral Approach," *Eur f Cancer,* 1990, vol. 26, No. 5, pp. 551–553.

Chang et al., "Synergy between Preactivated Photofrin II and Tamoxifin in Killing Retrofibroma, Pseudomyxoma and Breast Cancer Cells," *Eur f Cancer,* 1991, vol. 27, No. 8, pp. 1034–1038.

Doiron, D., "Instrumentation for Photodynamic Therapy,": *Laser Systems for Photobiology and Photomedicine,* 1991, pp. 229–230.

Chanh et al., "Preactivated Merocyanin 540 Inactivates HIV-1 and SIV: Potential Therapeutic and Blood Banking Application," *J. of Acquired Immune Deficiency Syndrome, 1992, pp. 188–195.*

Kirpal et al., "Preactivation: A New Concept for Generation of Photoproducts for Potential Therapeutic Applications," *Seminars in Surgical Oncology,* Jul./Aug. 1992, vol. 8, No. 4, pp. 250–253.

Ma et al., "Effects of Light Exposure on The Uptake of Photofrin II in Tumors and Normal Tissues," *Int. J. Cancer,* 1992, vol. 52, pp. 120–123.

Pervaiz et al., "Protein Damage by Photoproducts of Merocyanine 540," *Free Radical Biology & Medicine,* 1992, vol. 12, pp. 389–396.

Labrousse et al., "Photodynamic Killing of *Dictyostelium discoideum* Amoebae Mediated by 4', 5'-Diiodofluorescein Isothiocyanate Dextran. A Strategy for The Isolation of Thermoconditional Endocytosis Mutants," *Photochemistry and Photobiology,* 1993, vol. 67, No. 3, pp. 531–537.

Lytle et al., "Light Emitting Diode Source for Photodynamic Therapy," *SPIE,* 1993, vol. 1881, pp. 180–188.

Schlager et al., "Immunophototherapy for The Treatment of Cancer of the Larynx," *SPIE,* 1993, vol. 1881, pp. 148–158.

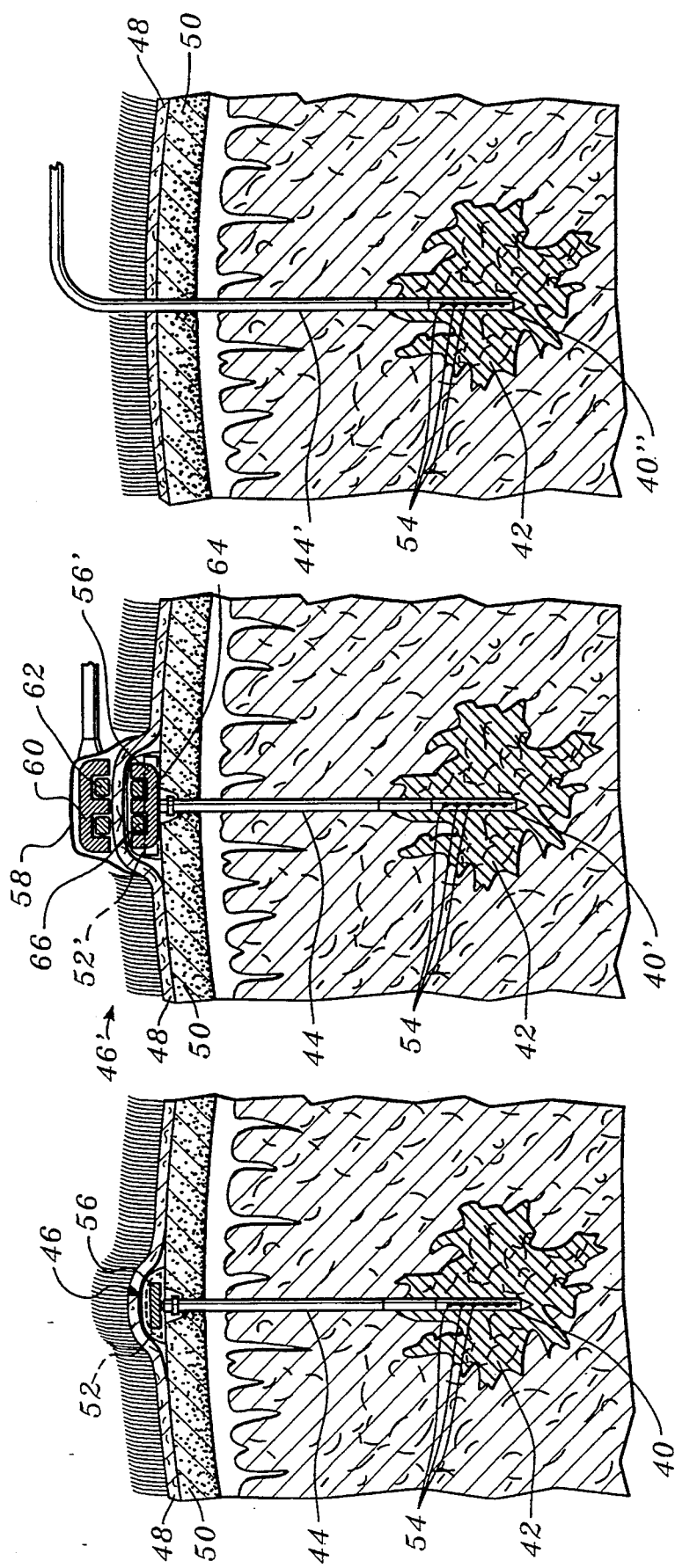

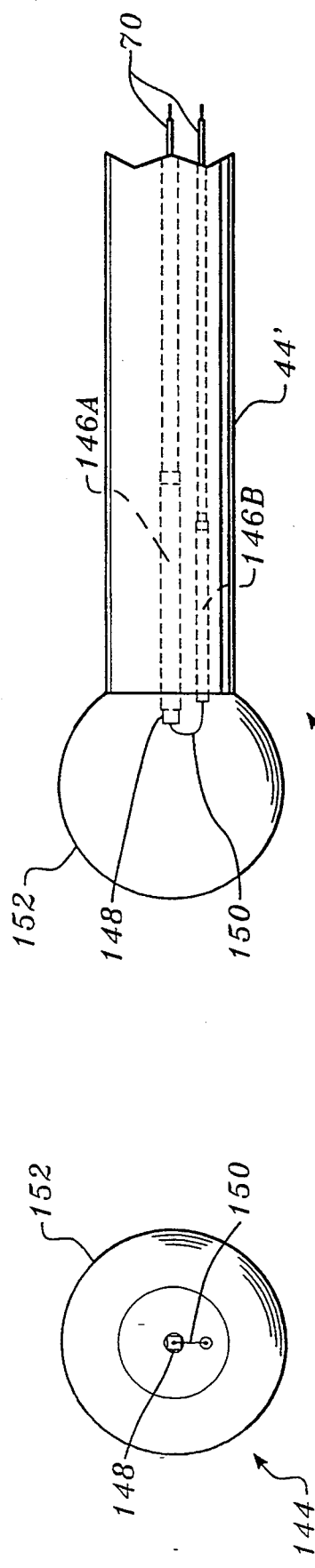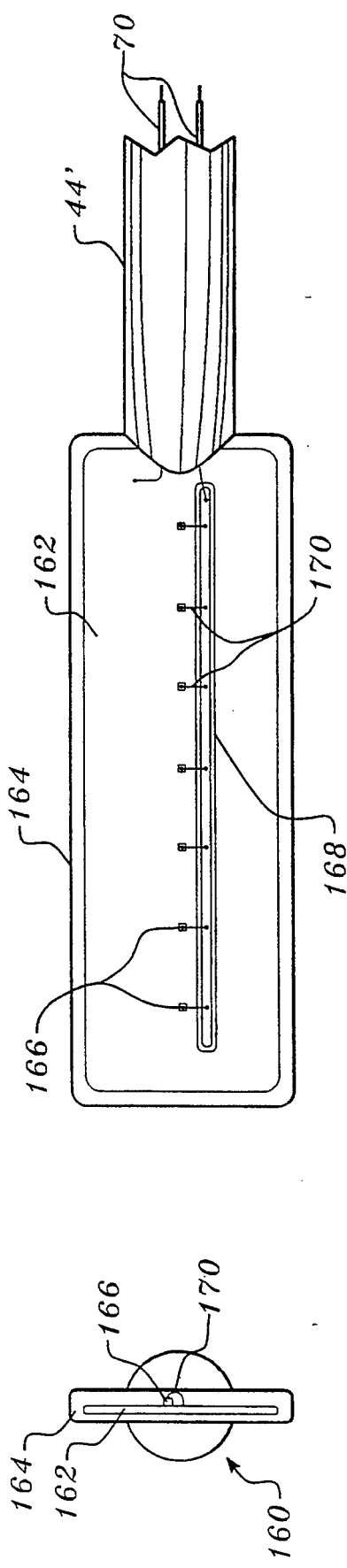

METHOD AND APPARATUS FOR PROVIDING LIGHT-ACTIVATED THERAPY

FIELD OF THE INVENTION

This invention generally relates to a method and apparatus for photodynamic therapy of tissue by light irradiation, and more specifically, to a method and apparatus for supplying light to a treatment site that has selectively absorbed a photoreactive agent perfused into it, for example, to selectively destroy cancerous cells.

BACKGROUND OF THE INVENTION

A tumor comprising abnormal cells is known to selectively absorb certain dyes perfused into the site to a much greater extent than surrounding tissue. For example, tumors of the pancreas and colon may absorb two to three times the volume of certain dyes, compared to normal cells, and intracranial gliomas show up to a 28 times level of absorption. Once pre-sensitized by dye tagging, the cancerous or abnormal cells can be destroyed by irradiation with light of an appropriate wavelength or waveband corresponding to an absorbing wavelength or waveband of the dye, with less damage to normal tissue. This procedure, which is known as photodynamic therapy (PDT), has been clinically used to treat metastatic breast cancer, bladder cancer, lung carcinomas, esophageal cancer, basal cell carcinoma, malignant melanoma, ocular tumors, head and neck cancers, and other types of malignant tumors. Because PDT may be selective in destroying abnormal cells that have absorbed more of the dye, it can successfully be used to kill malignant tissue with less effect on surrounding benign tissue in the brain and other critical areas.

Typically, invasive applications of PDT have been used during surgical procedures employed to gain access to a treatment site inside the body of the patient. Relatively high intensity light sources are used, to reduce the duration of the treatment, and thus the time required for the surgery, and because the majority of the prior art teaches that very high intensity light will more likely kill all of the malignant cells. Optical fibers in a hand-held probe are often used to deliver the intense light to the surgically exposed treatment site from a remote source, to reduce damage to surrounding tissue from the heat developed by the light source. High power lasers or solid state laser diode arrays in a remote light source coupled to the optical fibers are normally used for the light source. A typical prior art light source for PDT would provide from about 0.10 to more than 1.0 watts of optical power to achieve the high intensity, short duration exposures that are preferred. Because of the relatively high light intensity and power required to achieve it, apparatus to provide PDT is often too physically large and too heavy to be readily moved about with the patient.

The theoretical basis behind PDT is that the light energy absorbed by dye molecules in the malignant cells is transferred to dissolved oxygen to produce a reactive species called "singlet oxygen." This highly reactive form of oxygen kills cancer cells and damages tumor vasculature. Since the concentration of dissolved oxygen in cells is comparatively low, it is possible that after all available oxygen is activated and/or reacted with the cell materials, any additional increase in light intensity will have a negligible incremental effect on the tumor or in killing malignant cells. The limiting factor on the rate of malignant cell death in PDT may well be the rate at which additional oxygen diffuses into the treatment site from surrounding tissue and through replenishment via the vascular system. Contrary to the teachings of most of the prior art, the effectiveness of each photon of light impacting the treatment area may be highest at *very low light intensities,* over extended treatment times, and the optical efficiency may in fact decrease with increasing exposure level.

Several researchers, including Haas et. al., have shown that the level of cytotoxicity in photodynamic therapy appears to be proportional to the product of the integrated light exposure and the photoreactive agent's concentration, rather than to the instantaneous light intensity. In other words, the degree of PDT response is dominated by the total amount of light absorbed by the photoreactive agent over the treatment period. It can therefore be argued that if: (a) the photoreactive agent's concentration in the target tissue is maintained at a therapeutic level, and (b) apparatus for delivering light of the proper wavelength to a treatment site over an extended period is available, then the benefits of PDT can be realized with a less aggressive and potentially less costly treatment carried out over a period of days to weeks. Longer treatment periods at lower dosage rates may have other benefits as well, since high dose rates continued over extended periods can result in adverse normal tissue response.

Maintenance of therapeutic photoreactive agent levels is not difficult. It is well-known that many PDT photoreactive agents have a long half-life in the human body. In some cases, it is necessary for the patient to avoid direct sunlight for up to 30 days to avoid sunburn or phototoxic side effects.

It has been shown possible, in certain cases, to obtain improved therapeutic results in PDT at a low light level. As reported by J. A. Parrish in "Photobiologic Consideration in Photoradiation Therapy," pp. 91–108, *Porphyrin Photosensitization,* Plenum Press, (1983), preliminary laboratory studies with hematoporphyrin and visible light suggest that the reciprocity effect does not always hold, and that low light intensity may be more effective in PDT, in an absolute sense. In these experiments, subcutaneous tumors in the flanks of newborn rats were treated with the same external dose of 620 nm radiation at intensities of 7.5, 28, and 75 $mW/cm^2$. At the same total light dosage, Parrish found that greater tumor necrosis occurred at the lowest light intensity used.

In addition, several researchers have shown that combinations of certain photoreactive agents and low light levels exhibit very potent cytotoxicity. For example, Nitzan et. al. have shown that more than 99% of gram-positive *Staphylococcus aureus* and *Streptococcus faecalis* bacterial cultures can be killed with the application of 5 $mW/cm^2$ of broad band light from a tungsten bulb for 30 minutes, if the cultures are initially dosed with 1–10 micrograms/ml of deuteroporphyrin. Continued application of light for 10–11 hours results in a sterile condition in the culture, i.e., no bacteria remain alive.

Labrousse and Satre have demonstrated a similar photodynamic extermination of amoebae when dosed with low concentrations of 4'5'-Diiodofluorescein isothiocyanate dextran and irradiated for about 30 minutes with broad band light of 8–10 $mW/cm^2$ from a tungsten lamp. Both of these experimental results are particularly significant because the fraction of a tungsten lamp's output energy that can be absorbed by either photoreactive agent is small, since each agent has a narrow absorbance waveband.

For all PDT light sources, the vast majority of the optical power delivered to tissue eventually degrades to heat. From a therapy perspective, it is likely that this heat load will augment the treatment due to improved chemical reaction rates at higher tissue temperatures. It is also true that cells kept above approximately 43° C. are not viable. This effect is, in fact, used in the treatment of cancer using hyperthermia. In that situation, an attempt is made to heat the target tumor with radio frequency energy to a temperature on the order of 43°–45° C., while maintaining surrounding healthy tissue below 43° C. Combining hyperthermia with conventional transcutaneous PDT has been shown by B. Henderson et al. to increase the efficacy of both treatments (see "Interaction of Photodynamic Therapy and Hyperthermia: Tumor Response and Cell Survival after Treatment of Mice in Vivo," *Cancer Research*, Vol. 45, 6071 (December 1985)). Combining hyperthermia treatment with PDT delivered, for example, by an implantable probe in accordance with the present invention, will very likely augment the effects of either treatment used alone in destroying tumors.

A wide range of therapeutic benefits may be realized with the apparatus and methods of the present invention, beyond destroying tumors. These benefits include, but are not limited to, the destruction of other abnormal cell types, the destruction of normal tissue for therapeutic ends, selective destruction of pathogenic microorganisms, viruses, and other self-replicating disease agents, treatment of vascular or hematologic disorders, reducing or controlling inflammation, and the enhancement of normal cellular function, such as wound healing or immunologic response. It is contemplated that the PDT apparatus and methods disclosed below can be applied to providing such therapeutic benefits in both plants and animals.

Development of a method and apparatus for delivering light with an implantable probe, for extended periods of time, well beyond that available during the time that a patient's subdermal system is exposed during surgery, is therefore desirable. The prior art does not teach the benefits of the long term exposure using light provided by an *implanted light source* and therefore does not disclose an appropriate method or apparatus for administering such treatment. The benefits and advantages of this procedure and of the apparatus disclosed herein that was developed to effect the technique will become evident from the following Description of the Preferred Embodiments and the attached drawings.

SUMMARY OF THE INVENTION

In accordance with the present invention, a method for photodynamic treatment at an internal, in vivo treatment site to cause a desired therapeutic change comprises the step of applying a photoreactive agent that is selected for its characteristic wavelength(s) or waveband(s) of light absorption to the internal, in vivo treatment site. A light source having one or more emission wavelengths or wavebands substantially equal to an absorbing wavelength or waveband of the photoreactive agent is then positioned internally within a patient's body. Light emitted from the light source is then administered directly to the internal, in vivo treatment site and is absorbed by the photoreactive agent, which causes the desired therapeutic change at the treatment site.

In one embodiment of the method, the step of positioning the light source preferably comprises the step of providing a catheter having a distal end and a proximal end; the light source is disposed at the distal end of the catheter. The catheter and the source of light are moved into a patient's body, and the catheter is positioned so that its distal end and the light source are disposed proximate to the internal, in vivo treatment site. The catheter may include at least one lumen that extends generally between the proximal and distal ends of the catheter. A supply of the photoreactive agent can then be caused to flow through said at least one lumen so that it perfuses the internal, in vivo treatment site at the distal end of the catheter.

In another embodiment, the step of positioning the light source comprises the steps of invasively disposing the light source proximate to the internal, in vivo treatment site inside a patient's body, and leaving the light source in the patient's body while administering light to the treatment site, until the desired therapeutic change has occurred. Invasively disposing the source within the patient's body, in one form of the invention, includes the steps of causing a penetration of the patient's body to access the internal, in vivo treatment site, and then closing the penetration, leaving the light source implanted within the patient's body while the therapeutic treatment is performed. In one embodiment, the step of providing the light source comprises the step of providing at least one LED, and the step of invasively disposing the light source comprises the step of disposing the at least one LED proximate to the internal, in vivo treatment site, to illuminate the treatment site with light emitted by the at least one LED. Alternatively, the step of providing the light source comprises the step of providing at least one solid-state laser diode (LD), and the step of invasively disposing the light source comprises the step of disposing the at least one LD proximate to the internal, in vivo treatment site to illuminate the treatment site with light emitted by the at least one LD.

In the embodiments where the light source is coupled to the distal end of a catheter that includes at least one lumen extending generally between the proximal and distal ends of the catheter, the method further includes the step of providing an external power supply and electrical conductors that are connected to the power supply. Electrical current from the external power supply is then conveyed through the electrical conductors within the lumen(s) to energize the light source.

In the form of practicing the method wherein the light source comprises at least one LED or LD, the method further includes the step of periodically monitoring a temperature of the treatment site by determining a voltage-current characteristic of the LED(s) or LD(s) during a time when the LED(s) or LD(s) are not producing light, which yields a temperature of surrounding tissue, or immediately after or while the LED(s) or LD(s) are producing light, which yields a temperature of the light source.

It is contemplated that the method may optionally include the step of electromagnetically coupling an external source of power to the source of light to provide electrical current used by the light source. Alternatively, the method can include the step of providing a self-contained power source that is disposed with the light source, within the patient's body, to energize the light source.

A further step in the method is to heat the treatment site to improve the efficacy of the photodynamic treatment. The step of heating may then comprise the step of using waste heat from the source of light that is disposed proximate to the treatment site. The method can also include the step of measuring a physiological parameter at the treatment site to determine the efficacy of the photodynamic treatment.

Another aspect of the method is directed to periodically infusing the photoreactive agent into the treatment site. This step comprises the step of infusing the photoreactive agent through a catheter from at least one external reservoir. Alternatively, the photoreactive agent is infused from at least one reservoir that is disposed with the light source, inside the patient's body.

In another embodiment, the light source comprises a plurality of light sources, and the step of administering the light comprises the step of sequentially energizing selected ones of the plurality of light sources to illuminate different portion of the internal, in vivo treatment site, as the selected ones of the plurality of light sources emit light. Alternatively, the light sources can be selectively modulated to vary the intensity of light emitted by the light sources.

In yet another aspect of the present invention, the light source is optically coupled to a catheter that conveys the light emitted by the light source. The catheter has a proximal end and a distal end and comprises a material selected for its optical properties that enable it to conduct light. The proximal end of the catheter is optically coupled to the light source, so that the catheter conducts the light to its distal end, which is adapted for insertion into a patient's body, to be positioned at the internal, in vivo treatment site. Light conveyed by the catheter causes the desired therapeutic change. The exterior surface of the catheter has a different refractive index than the interior body of the catheter to ensure that the light is conveyed through the catheter and does not escape through the outer surface.

Apparatus for administering a photodynamic treatment at an internal, in vivo treatment site, to cause a desired therapeutic change is yet another aspect of the present invention. The apparatus includes elements that perform functions generally consistent with the steps of the method discussed above.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2A is a cut-away view of a first embodiment of a light source implanted at a treatment site;

FIG. 2B is a cut-away view of a second embodiment of a light source implanted at a treatment site and configured to be inductively coupled to a source of external power;

FIG. 2C is a third embodiment of the light source that is coupled to an external power source through a flexible catheter;

FIGS. 10A and 10B are side and end views, respectively, of an alternative embodiment for an implantable probe;

FIGS. 11A and 11B are top and end views, respectively, of another embodiment for an implantable probe;

DETAILED DESCRIPTION OF THE PREFERRED EMBODIMENT

Experimental Proof of PDT Efficacy Using Low-Intensity Light

A basic premise underlying the present invention is that exposure of a treatment site that has been perfused with an appropriate photoreactive agent, to relatively low intensity light for an extended period of time, provides a therapeutic benefit comparable to more conventional PDT in which the treatment site is exposed to relatively high intensity light for a relatively short period of time.

Figure 1:
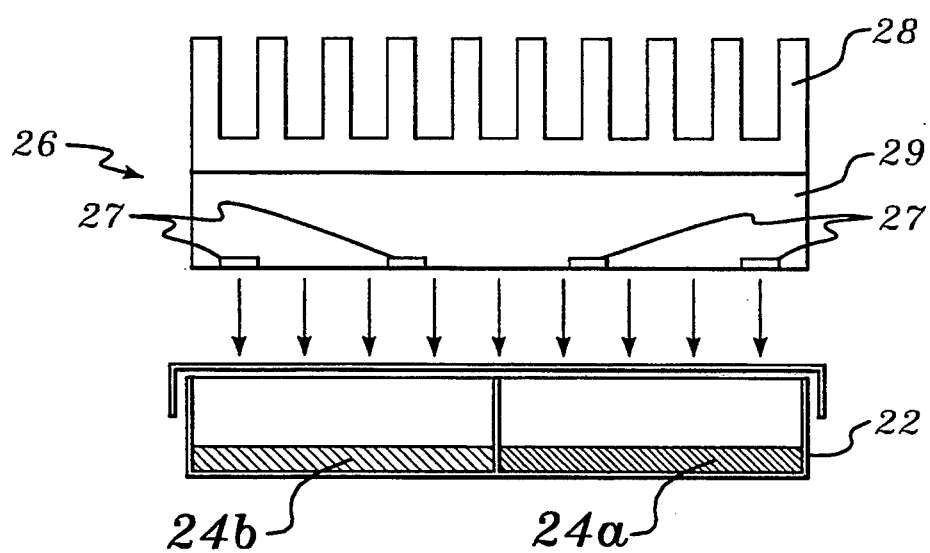
FIG. 1 illustrates the apparatus used in a laboratory test to determine the efficacy of photodynamic treatment in accordance with the present invention.

Further confirmation of low dose rate efficacy was obtained with the following in vitro PDT experiment, conducted with the apparatus shown in FIG. 1. In these tests a low intensity light source 26 was used comprising a 4×4 array of discrete LEDs 27 (Stanley Electric Co. Model FH1011, having a peak emission wavelength of 660 nm) embedded in a flat metal plate 29. This plate was attached to a tinned heat sink 28 to dissipate waste heat produced by the LEDs to the surrounding air. When operated at a nominal drive voltage of 2.2 volts, the LEDs produced approximately 2.6 mW/cm$^2$ of light, measured at a plane 2.5 cm below the plate's base.

For efficacy testing, methylene blue was used as the photosensitizer reagent. Each half of an Agar-coated, two-pocket Petri dish 22 was inoculated with an equal quantity of *Staphylococcus epidermidis* bacteria and then the left half was charged with 0.5 ml of a buffer 24a, while the right half was charged with a similar quantity of a buffer 24b, dosed with 5 micrograms/ml of methylene blue. The entire surface area of this two-pocket Petri dish 22 was then irradiated with light from the array of LEDs at a flux density of 2.6 mW/cm$^2$. A second substantially identical two-pocket Petri dish (not shown) was similarly inoculated and photosensitizer dosed, but was thereafter wrapped in aluminum foil and not exposed to light. After incubation of both Petri dishes at 37° C. for 14 hours, heavy bacterial growth was noted in all Petri dish sections except the one section continuously irradiated over the incubation period with LED light and containing methylene blue, where no growth occurred. This experiment was repeated several times with identical results.

The preceding experiment shows that relatively long exposure of photoreactive agent-sensitized bacterial cells to light of much lower intensity than clinically used will destroy bacterial cells. It is believed that the same effective results would be obtained in connection with PDT of photoreactive agent-perfused tissues or body fluids, with relatively low intensity light, for relatively longer periods of time—compared to more conventional PDT.

Description of implantable Probes Used for PDT

Given the proof of principle provided by the above described experiments, it is apparent that a low cost, compact implantable delivery device for providing low intensity light to a treatment site for an extended period of time is required to facilitate commercial practice of this technique. Instead of being forced to rely upon a relatively high intensity light source for irradiating a tumor or other treatment site perfused with a photoreactive agent during the limited time the site is surgically exposed, a medical practitioner would then have the option of implanting a probe that either includes a low intensity light source in the implantable probe or that employs an optical fiber to convey light from an external low intensity source to an implantable probe. Of course, use of an implantable probe is not limited to a low intensity light source, since it is also contemplated that a relatively high intensity implanted light source might be periodically pulsed on for short duration exposures of the treatment site. The implantable probe is invasively positioned at the treatment site during a surgical procedure that opens the treatment site or provides access to a patient's internal systems, e.g., by an incision allowing insertion of the implantable probe into the cardiovascular system and then left in place after the surgeon has closed the incision adjacent the treatment site. The photoreactive agent is perfused into the treatment site, either during the surgical procedure or after the implantable probe is positioned in place. Light emitted from the implantable probe then irradiates the photoreactive agent perfused treatment site, either on a continuous basis or intermittently, typically for at least several hours, and perhaps, for several days or weeks. Additional photoreactive agent is perfused into the treatment site as required.

For purposes of this disclosure and the claims that follow, the term "photoreactive agent" is defined as a solution comprising at least one photoreactive species or at least one precursor photoreactive species, where the solution may also include other reagents or medications that augment the photodynamic treatment. For example, it may be desirable to adjust the pH of the treatment site by perfusion with a solution including a photodynamic species buffered to a particular pH, or, with a solution that includes a photodynamic species in combination with antibiotics and other medications that minimize secondary reactions or improve the treatment efficacy.

It is also possible that all photoreactive species in the solution do not have optical activity at the same wavelength or wave band. The use of either an internal or external array of light sources also allows incorporation of LEDs or LDs operating at two or more wavelengths or wavebands, and the ability to selectively activate the LEDs or LDs operating at a given wavelength or waveband as desired, so that light at the different wavelengths or wavebands is provided to the treatment site either sequentially or simultaneously from the light source. Such multiwavelength/waveband light source options can provide a clinician with PDT treatment modalities not possible with existing single wavelength or waveband light sources.

It may also be desirable to perfuse the treatment site with solution containing dissolved photodynamic species that do not activate oxygen, but instead, have other mechanisms for providing the therapeutic change that is desired. As an example, the treatment site can be perfused with solution containing a photodynamic species that absorbs light at wavelengths much longer than those that are effective in activating oxygen. Certain of such species, known for their characteristic absorption of light at long wavelengths, i.e., in the 700 to 1500 nm range, have large and extended molecular orbitals that can cause the species to exhibit thermal- and photo-instability. If these precursor species are perfused into the treatment site and are then broken into fragments by irradiation with long wavelength light, possibly in combination with heat, the resulting free radicals or smaller molecular species formed may be particularly effective therapeutic agents.

Because of the likely high reactivity and the relatively short lifetime of the free radicals and smaller molecules into which the precursor species break down, it may not be practical to irradiate the precursor species to initiate the breakdown before the precursor species are infused into the treatment site. Instead, it is more likely that the photodynamic treatment must be administered to activate the precursor species after perfusion into the treatment site. Examples of precursor species that absorb long wavelength light and are expected to exhibit PDT activity include long-chain cyanine dyes, dimers of phthalocyanine dyes, and one-dimensional conducting polymer chains.

Since infrared light penetrates more deeply into tissue than visible light, it is contemplated that an infrared light source could be used to augment the photodynamic treatment, allowing fewer and more; widely distributed light sources to activate the precursor species at the treatment site.

Three different configurations for the implantable probe system are disclosed in FIGS. 2A through 2C. In these and subsequent figures, elements of the invention that have a common function, but a different shape or configuration are identified by the same numeric reference numeral, distinguished from each other by the addition of a ′ or ″ notation. For example, in FIG. 2A, an implantable probe 40 is illustrated as used for treating a malignant brain tumor 42, while in FIG. 2B, an implantable probe 40′ is shown, and FIG. 2C shows an implantable probe 40″. In each of these three different configurations of the implantable probe system, an array 54 of LEDs are disposed within the implantable probe and these LEDs are provided with electrical power through leads (not shown), which extend through a flexible catheter 44 (or through a flexible catheter 44′ in the embodiment of FIG. 2C). In this and most other embodiments of the implantable probes, it is contemplated that solid-state laser diode (LDs) chips could be used instead of the LEDs as the source of the light. Implantable probe 40 in the first of these three figures includes a head 46 that is disposed on a proximal end of flexible catheter 44, for example, between a patient's scalp 48 and skull 50. Inside head 46 of the device are disposed an LED (or LD) drive module 56 and an optional photoreactive agent reservoir 52 that holds a photoreactive agent that is periodically perfused through flexible catheter 44 into malignant brain tumor 42 during the extended exposure of the treatment site to light from the LEDs. Optionally, additional reservoirs like photoreactive agent reservoir 52 may be provided to supply multiple component photoreactive agents, PDT augmenting agents or medications, and other fluids to the treatment site.

To simplify this disclosure, the following discussion specifically references LEDs and the LED drive module; however, it will be understood that the description also applies to LDs or to an array of LDs (as appropriate), and to LD drive modules. Generally, any use of the term "LED" in the discussion of these elements can be replaced with "LD," except where specifically noted.

Electrical power for the LEDs or LDs can be obtained using several approaches, any one of which are applicable to either type of light source. For relatively short exposures, a small battery storage (not separately shown) within LED drive module 56 provides the electrical power for array 54. For longer exposure PDT, as shown in FIG. 2B, implantable probe, 40′ has a head 46′ that includes an LED drive module 56′. In LED drive module 56′ is a secondary transformer core 64 and a secondary winding 66 that can be inductively coupled transcutaneously to a power pack 58. Power pack 58 includes a primary transformer core 60 and primary winding 62 that is electrically connected to a source of alternating or pulsating current (not shown). The current induced in secondary winding 66 is rectified and coupled to LED array 54. An optional photoreactive agent reservoir 52′ is included in head 46′ for infusing additional photoreactive agent into the treatment site during the PDT.

Electrical power at shorter wavelengths could also be coupled into an implantable probe by using a microwave emitter (not shown) that is outside of the patient's body to transmit microwave power to art antenna array (not shown) that is implanted in the patient's body and electrically coupled to the LEDs on the probe. Power at optical wavelengths can be electromagnetically coupled from an external infrared light source to a infrared sensitive photodetector that is implanted in the body. The method used for supplying electrical power to the implantable probe will be influenced by the required power transfer efficiency, hardware cost, and convenience to the patient.

Flexible catheter 44′ in the third alternative embodiment of implantable probe 40″, shown in FIG. 2C, penetrates the scalp of the patient and is coupled to an external source of DC and to an external photoreactive agent source (neither shown). Photoreactive agent from the external photoreactive agent source is perfused into the treatment site through flexible catheter 44″ during the PDT, as needed. Each of the embodiments of the implantable probe shown in FIGS. 2A through 2C has advantages and disadvantages. For example, implantable probe 40″ can be in place the longest, since the quantity of photoreactive agent available for perfusion and the electrical power needed to energize the LED array is not limited by a battery, as in implantable probe 40. However, implantable probe 40″ must be coupled to an external source of power and photoreactive agent, making it less convenient to activate the PDT while a patient is ambulatory. Similarly, LED array 54 in implantable probe 40′ is only activated when the external power pack is positioned over head 46′, which may impact on the freedom of the patient to move about during the PDT.

The duration of PDT required depends on many variables relating to the therapeutic application, such as the shape and size of the treatment site, and the rate that oxygen or other reactants infuse into it and the rate that products of the reaction diffuse out of the treatment site. Generally, the treatment period is selected to optimize the optical efficiency, as a function of these criteria.

Figure 3A:
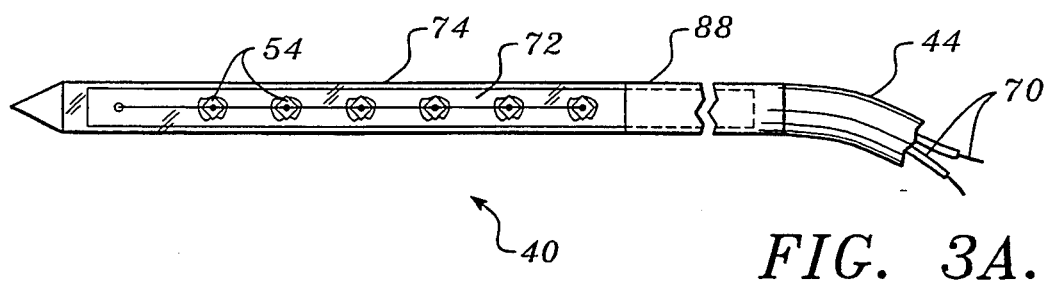
FIGS. 3A, 3B, and 3C are respectively a cut-away top view of an implantable probe, a cut-away side view of the probe, and an exploded view of a portion of the side view showing an LED mounted in the implantable probe.
Figure 3B:
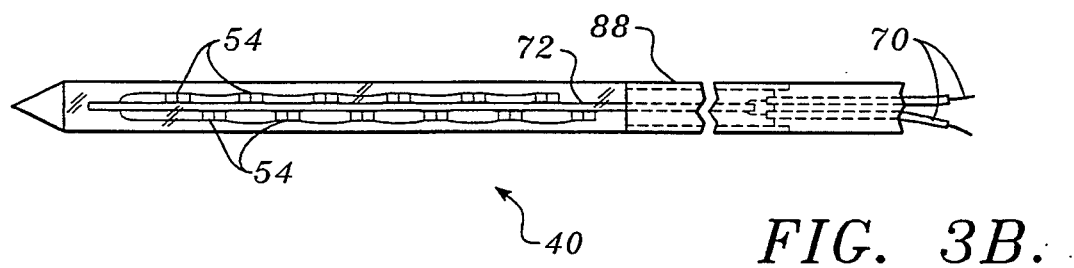
Figure 3C:
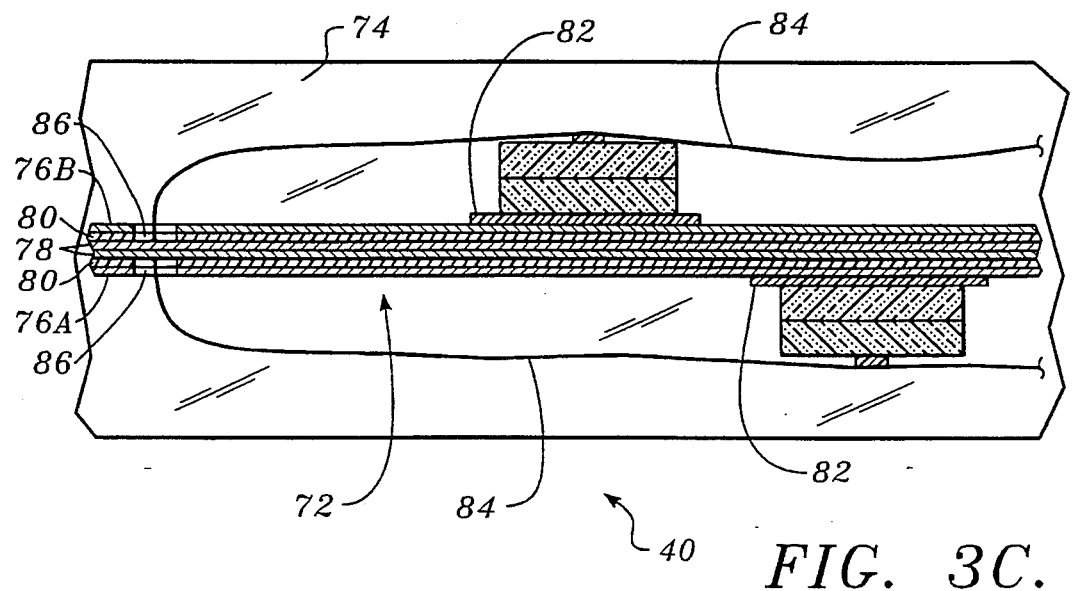

Details of the internal construction of implantable probe 40 are shown in FIGS. 3A through 3C. It should be noted that implantable probes 40′ and 40″ can be similarly configured. Each of the LEDs comprising LED array 54 are preferably about 0.2 to 0.3 mm square and 0.2 to 0.25 mm high and are mounted onto the top and bottom faces of a multi-layer planar light bar 72, about 1.5 to 3.5 mm apart. Multi-layer planar light bar 72 comprises alternating layers of conductive foil 76/78 and an insulating film 80, as shown most clearly in the enlarged view of a portion of the implantable probe presented in FIG. 3C. Alternatively, LED array 54 can be disposed on only one side of light bar 72, requiring, for example, only conductive foil layers 76a and 78, separated by insulating film 80. Materials used for manufacturing flexible printed circuit boards are suitable for use as the conductive foil layers and insulating film. One side of light bar 72 might comprise two layers of 0.019 mm thick copper (conductive foil layers 76a and 78) bonded to each side of a 0.038 mm thick polyamide film core (insulating film 80). It is preferred that a mechanically soft metal be used for the conductive layers, such as copper, gold, silver, or alloys thereof. Strips of commercially available laminates, such as DuPont Electronic's flexible double-sided PC circuit board material, "Pyralux" Type LF7022, which comprises an insulating polyamide film having copper foil laminated on opposed faces can be used for light bar 72.

In the preferred form of the implantable probe illustrated, the LEDs comprising 2LED array 54 are bonded to conductive foil layer 76a on one face of light bar 72 and to a conductive foil layer 76b on the opposite face of the light bar, using a conductive adhesive 82. Conductive foil layers 76a and 76b are both electrically connected in common to one of power leads 70. The other power lead is electrically coupled to two conductive foil layers 78, which are joined back-to-back and extend longitudinally down the center of light bar 72. Leads 84 are electrically connected to conductive layers 78 exposed at apertures 86 that ;are disposed adjacent the distal end of the implantable probe. Apertures 86 are made by first etching away conductive foil layers 76a and 76b using an appropriate photoresist image and a conventional PC board etchant, followed by a polymer etch performed with a gas plasma. For the plasma etch procedure, the conductive foil layer forms a natural mask. By using gold wire bonding techniques that are conventional in the semiconductor industry, all LEDs can be connected together by leads 84 on their top side, as shown.

Preferably, the LEDs comprising LED array 54 are coupled in parallel between conductive foil layers 76a or 76b and leads 84, but they could alternatively be connected in series by appropriately modifying the conductive foil and wire configuration. Each of the serial and parallel wiring configurations has advantages and disadvantages. A parallel connection reduces the voltage needed to drive the LED array, whereas a series connection assures that each LED in the LED array will carry the same drive current and emit approximately the same quantity of light.

Light bar 72 is encapsulated in an electrically insulating, light diffusing semitransparent polymer 74 that protects the LEDs from body fluids and insulates the layers of conductive foil 76/78 that convey electrical power to the LEDs. When current flows through the LEDs comprising LED array 54, light is generated and emitted through the top and side walls of the LEDs, passes through semitransparent polymer 74, and irradiates the surrounding tissue, for example, at treatment site 42.

To ensure a comparatively uniform spatial light output from LED array 54, semitransparent polymer 74 incorporates a small amount of an optical diffusant. A typical diffusant that can be employed for this purpose, being normally used in optical epoxies, is LED-101C, manufactured by Transene Co., Inc. of Rowley, Mass.

Implantable probe 40 may be joined to flexible catheter 44 by a cylindrically shaped thermally conductive transition piece 88. The significance of transition piece 88 in connection with hyperthermally augmenting the PDT will be apparent from the discussion below that covers that aspect of the invention. Not shown is a lumen that extends through flexible catheter 44, and ports disposed in the transition piece in fluid communication with the lumen, for conveying photoreactive agent from photoreactive agent reservoir 52 or 52' into treatment site 42 (see FIGS. 2A and 2B). However, the lumen and ports are similar to a lumen 182 and ports 184 that are shown in FIG. 12C in connection with another embodiment of the implantable probe.

A light bar 108 having a different configuration than light bar 72 is shown in FIGS. 7A through 7D. Light bar 108, which is primarily for use with LEDs (not LDs), requires fewer LEDs to achieve uniform circumferential light emission than light bar 72. The light bar is illustrated inside implantable probe 40', but can also be employed in implantable probes 40 and 40". As clearly shown in FIG. 7C, light bar 108 comprises two conductive foil layers 110 and 112, which are respectively bonded to opposite sides of an insulating layer 114. A plurality of rectangular apertures 122 formed in spaced-apart array along the longitudinal axis of light bar 108 each define positions for mounting one of LEDs 120. To mount each LED 120, conductive foil layer 110 is masked and etched to define a tongue 116 that is folded down through one of apertures 122, at one end of the aperture. Conductive film layer 112 on the rear face opposite the tongue is removed at each aperture, as is the polymer film substrate comprising insulating layer 114 under the tongue. One LED 120 is bonded to each tongue 116 using a silver or gold-bearing epoxy or other electrically conductive adhesive. A gold bond wire 118 is then attached to the top face of the LED. Tongue 116 is bent downwardly so that the LED's terminal axis coincides with the longitudinal axis of light bar 108, and the free end of the gold wire is bonded to conductive film layer 112, on the underside of the light bar.

In the configuration of light bar 108, each LED 120 emits light on both sides of the light bar 108, eliminating the need for providing additional LEDs (mounted on opposed faces of the light bar), as required with the first design, and potentially allowing a smaller diameter implantable probe to be constructed. However, this design is somewhat less efficient than light bar 72, since light bar 108 obstructs light emission parallel to its plane.

Figure 7A:
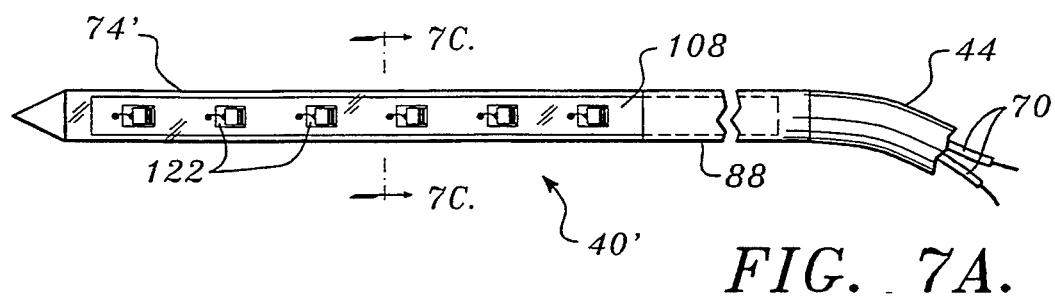
FIGS. 7A, 7B, 7C, and 7D are a cut-away top view, side view, cross-sectional view (taken along section lines 7C—7C), and an exploded view, respectively, of another embodiment of an implantable probe for providing PDT.
Figure 7B:
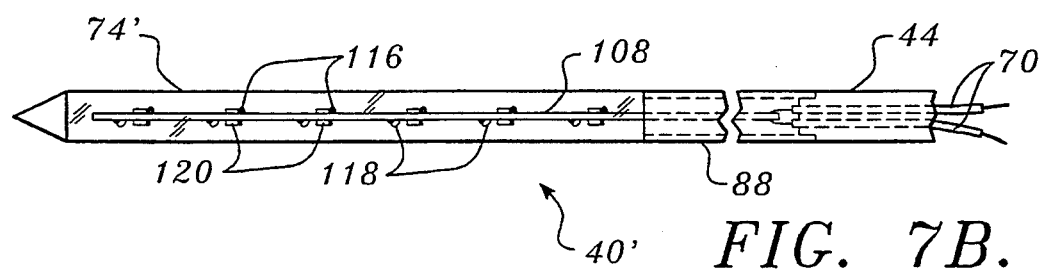
Figure 7C:
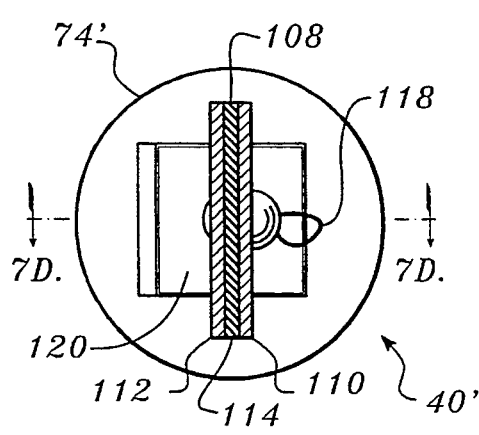
Figure 7D:
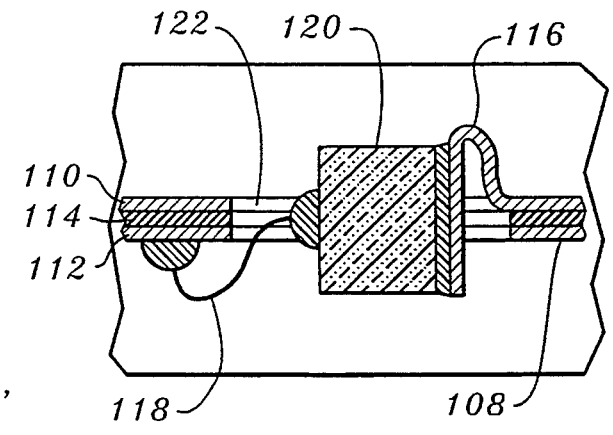
Figure 7E:
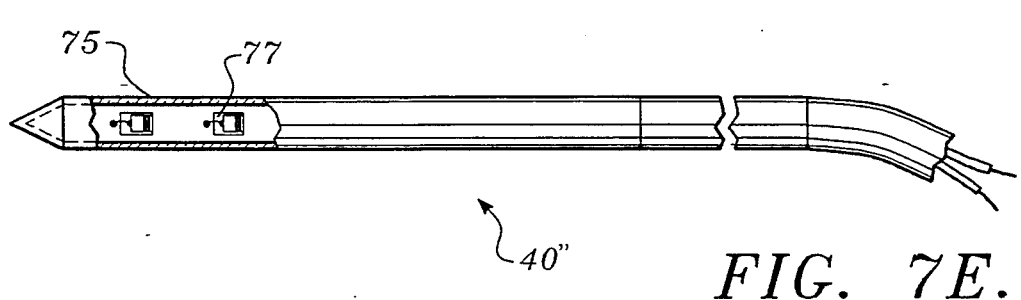
FIG. 7E is a cut-away top view of an embodiment of an implantable probe like that of FIGS. 7A through 7D, but constructed using a transparent ceramic tube.

FIG. 7E illustrates light bar 108 in an embodiment of implantable probe 40" that includes an external polycrystalline ceramic tube 75. Again, this same element could be employed in implantable probes 40 and 40'. The interior volume of ceramic tube 75, around light bar 108, is filled with a transparent polymer 77. An appropriate ceramic is selected for the ceramic tube to act as a light diffuser, heat transfer interface to the surrounding tissue, and electrically-insulating shroud around light bar 108. For example, aluminum oxide-based ceramics could be used for the ceramic tube, since they have thermal conductivities on the order of stainless steel and diffuse light very well because of their fine-grained microstructure. Electrical breakdown strengths for such materials are also very high.

Each of the implantable probes disclosed above can optionally include circuitry for selectively multiplexing the light sources provided on the probe, so that less than all of the light sources are energized at one time. A desired geometrical pattern of light can thereby be provided by the implantable probe on the treatment site. Further, the intensity of each light source can optionally be selectively controlled so that less than full rated intensity is developed by the light sources. These options are implemented by including appropriate multiplexing; and/or modulating circuitry in the probe, coupled between the power supply and the light sources. Further details are provided below, in connection with another embodiment on an implantable probe.

Benefits of Using LEDs for PDT

There are advantages to using LEDs in implantable probes 40, 40′, and 40″ as the source of light for the PDT instead of laser diodes. Laser diodes can be used in these devices, but because of their high sensitivity to operating temperature and the need to maintain their drive current within relatively narrow limits, a laser diode light source requires more careful design. When supplied electrical current below rated levels, laser diodes do not lase, while if supplied slightly higher than rated current, their operating life is severely shortened. Laser diodes are considerably more expensive than LEDs. In contrast, LEDs are comparatively simple devices that operate over much wider ranges of current and temperature. LEDs degrade to about half of the original output intensity over 100,000 hours—much longer than the hours or days during which the implantable probes will be used. Accordingly, change in output intensity of LEDs over the period of use in the PDT is not of any concern.

As will be explained in detail below, PDT can also be provided using light produced by an external source that is delivered to a treatment site through an optical fiber. However, providing LEDs within the implantable probe as a source of light eliminates the optical fiber link required by an external light source and ensures that substantially all of the light emitted by the array of LEDs is delivered to the treatment site.

LEDs have a relatively broad emission pattern wherein about one-half of the light is emitted through the side walls and the remainder through the top of the LED. As a result, it is difficult to concentrate all of the emitted light and direct it into the end of an adjacent optical fiber to deliver the light from an external source to an implantable probe at the treatment site. Typically, assuming a Lambertian LED emission pattern, an optical fiber may collect only about 36% of the emitted light. By comparison, virtually all of the light emitted by LEDs 120 in the embodiments of the implantable probe discussed above is available to activate the photoreactive agent perfused tissue at the treatment site.

Figure 4:
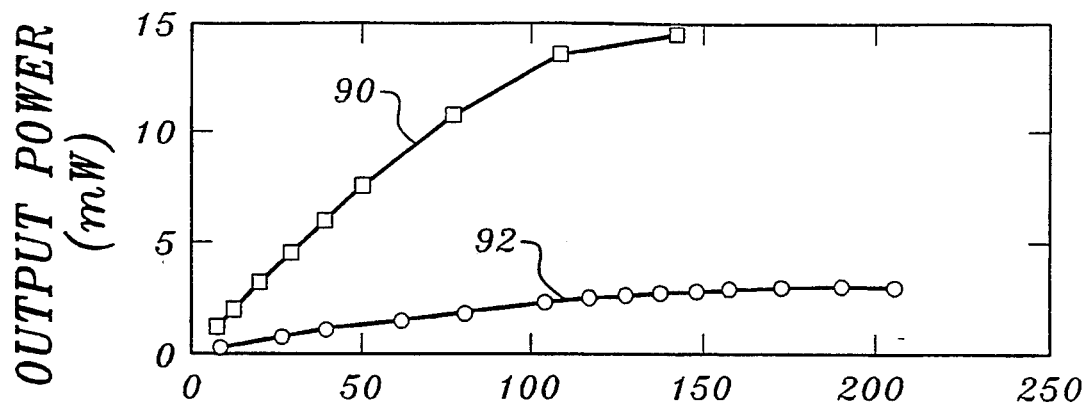
FIG. 4 is a graph of power output of a high current LED versus its drive current, for two operating conditions.

FIG. 4 illustrates the output light intensity of a bare LED (Stanley type FH1011) and that of the same LED mounted on a heat sink and coupled to a one mm diameter plastic optical fiber, in terms of output power (mW) and drive current (mA). In this evaluation, the output power of the devices was monitored using a photometer with integrating sphere manufactured by UDT Instruments. Comparison of line 90 for the bare LED and line 92 for the optical fiber show that at maximum output power, the output of the bare LED is above 14 mW and that of the optical fiber is about 3 mW. Coupling losses (coupling the LED to the optical fiber) are thus about 82%. A laser diode, being more directional, would have a typical coupling loss to an optical fiber of about 10%.

Figure 5:
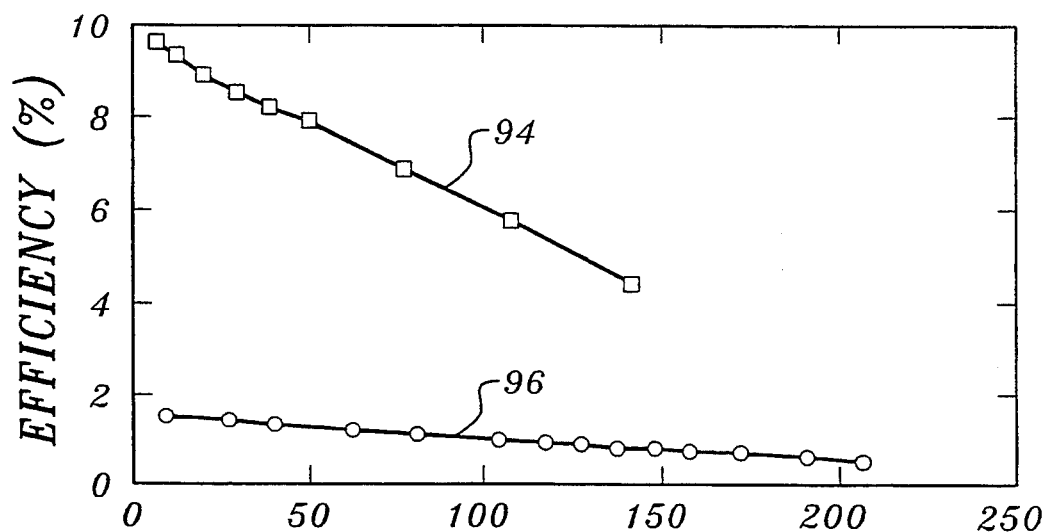
FIG. 5 is graph of optical efficiency :for both a bare LED and an LED transmitting light through an optical fiber.
Figure 6:
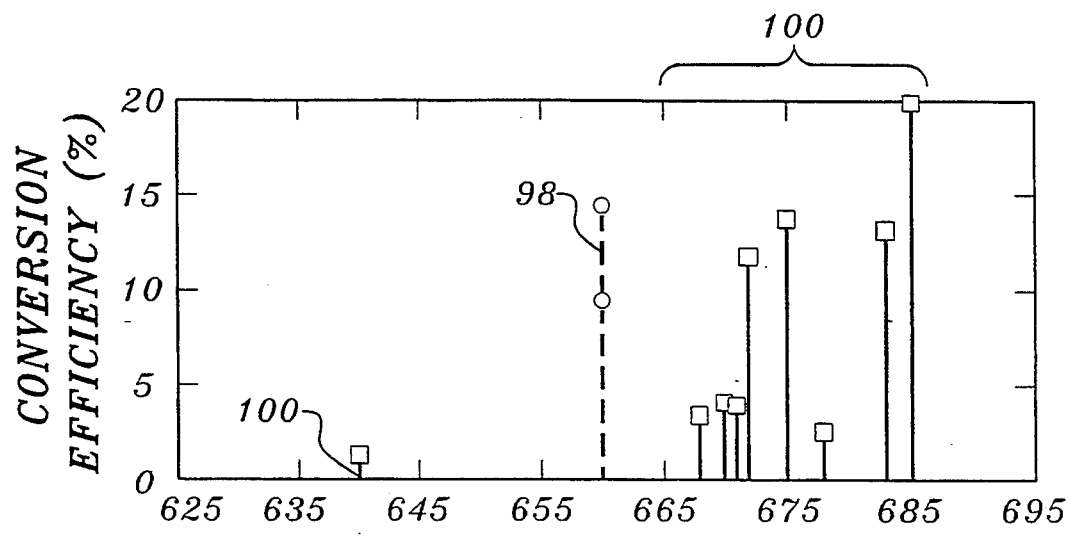
FIG. 6 is a graph comparing the operating efficiency and wavelength of several laser diodes and an LED.

FIG. 5 graphically compares the efficiencies of the bare LED (a curve 94) and the LED coupled to an optical fiber (a curve 96), discussed above. In FIG. 6, the electrical conversion efficiencies versus wavelength (nm) of laser diodes (Phillips type CQL800/D) represented by lines 100 are shown for comparison against that of an LED (Stanley type FH1011) represented by a line 98. Although the LED has a comparable conversion efficiency, it costs less than 1/100 as much as each laser diode. It is also apparent that LED development has not been directed toward reducing internal absorption and internal reflections at the device/air interface. Use of smaller LED devices can reduce these losses, and antireflection coatings can be used to increase the overall output efficiency of LEDs for the present application.

Hyperthermic Augmentation of PDT

Because the implantable probe is directly embedded in the tissue at treatment site 42, waste heat produced by LEDs 120 or corresponding LDs can be used in combination with their emitted light to augment the efficacy of the PDT. Calculations performed for a light bar with an outside diameter of about 1.5 mm and a heat output of 0.8 W/cm of length indicate a surface temperature for the implantable probe of 60°–90° C. (in poorly perfused tissue). This temperature is well above that needed to kill cells and may cause damage to normal cells. Since there is no comparable cancer treatment available at this time, there are also no empirical data as to the safe upper operating range for such a thermal-based cancer treatment. However, there are suggestions in the prior art concerning allowable heat flux levels that are relevant to this issue, as noted below.

Two genetic approaches are proposed for transferring and dissipating heat within the implantable probe. In the embodiments of the implantable probe shown respectively in FIGS. 3A through 3C, and in FIGS. 7A through 7E, the conductive foil layers comprising the outer faces of the light bar are extended into thermally conducting contact with transition piece 88 (made of metal), which is disposed immediately behind the light bar. Heat from each LED 120 is conducted down the conductive foil of the light bar to transition piece 88, which is then used as a heat transfer interface to surrounding tissue, e.g., in treatment site 42 (FIGS. 2A through 2C). In addition to careful sizing of the conductive foil layers to ensure adequate longitudinally axial thermal conduction, this approach requires good thermal contact between the light bar and the interior of the transition piece. The contact can be readily accomplished by ensuring the light bar is slightly wider than the I.D. of transition piece 88, creating an interference fit along the edges of the light bar. Heat transfer can be further augmented by backfilling the interior of the transition piece with a thermally conductive epoxy (not shown), or through light diffusing plastic encapsulation 74, which extends into the interior of transition piece 88.

In implantable probe 40″ shown in FIG. 7E, heat is dissipated more directly to surrounding tissue by ceramic tube 75, which is a better thermal conductor than the light diffusing plastic encapsulation used in the other embodiments of the implantable probe. Transition piece 88 is still optionally provided in implantable probe 88, but is not required for conducting waste heat to the surrounding tissue, since the ceramic tube is sufficient for that purpose.

Heat fluxes proposed here are broadly comparable to levels tolerated under certain in vivo conditions. A heat flux believed acceptable for the example discussed above is 1.7 W/cm$^2$ at the probe surface. In "Electron Enhancement of Photodynamic Action (EE-PA)," *Proc. of Conf. on Advances in Phototherapy* (1989), M. Schwartz and G. Clark disclose a test in which 0.112 W/cm$^2$ was delivered in a PDT protocol and indicate that the tumor temperature increased by less than 2° C. If this temperature rise is scaled relative to heat flux, then an exposure of 1.7 W/cm$^2$ should increase tissue temperature by 30° C. J. Feather et al., "A Method for the Construction of Disposable Cylindrical Diffusing Fibre Optic Tips," *Lasers in Medical Science*, Vol. 4, 229 (1989), indicate that an exposure of up to 1.1 W/cm² can be delivered to whole blood without damage. E. Laws et al., in "Photoradiation Therapy in the Treatment of Malignant Brain Tumors: A Phase I (Feasibility) Study," *Neurosurgery*, Vol. 9, (6), 672 (1981), describe the treatment of malignant brain tumors in which 0.3–0.4 watts of optical power were delivered to the tumor through an optical fiber. In their case, the power flux at the distal tip of the optical fiber was 23 W/cm². In that set of experiments, temperatures ranged from 76° C. at the fiber tip to 45° C. at a distance of 5 mm from the optical fiber.

The work of B. Henderson et al., "Interaction of Photodynamic Therapy and Hyperthermia: Tumor Response and Cell Survival after Treatment of Mice in Vivo," *Cancer Research*, Vol. 45, 6071 (December 1985), is particularly relevant and gives reason to believe that the implanted probes described herein may kill some types of tumor much more effectively than other PDT approaches, in part, because of the hyperthermia augmentation provided by waste heat developed by the LEDs or LDs on the light bar in the implanted probe. Henderson et al. describes a series of experiments in which a tumor line derived from radiation-induced fibrosarcoma was implanted in the right flank of C3H/Hej mice. Four different curative treatments were attempted. In one protocol, twenty mice were given a standard hyperthermia treatment in which the tumors were heated to 44° C. using localized microwave energy. In the second protocol, PDT (from an external light source) alone was administered to 60 mice, the treatment comprising exposure with light at 135 J/cm² intensity and with a wavelength of 630 nm delivered *transcutaneously* 24 hours after an injection with 10 mg/Kg of the photo sensitizer Photofrin II. In the third protocol, a hyperthermia treatment was administered to 20 mice followed by externally applied PDT. In the fourth treatment, externally applied PDT was administered to 40 mice, followed by hyperthermia. Finally, in a fifth ;protocol, the photosensitizer was administered to 20 mice 24 hours before hyperthermia treatment, but no PDT was provided.

Figure 8:
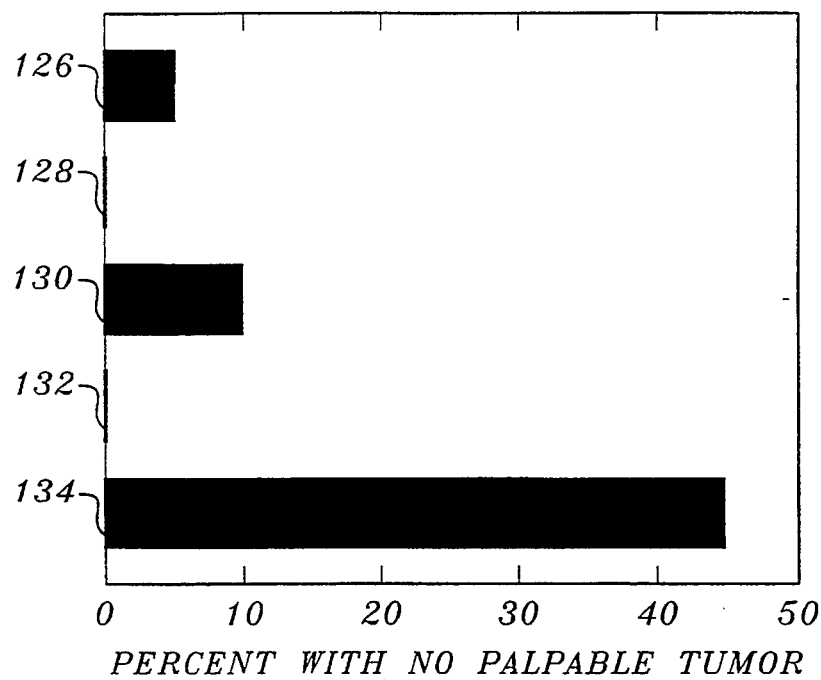
FIG. 8 is a (prior art) graph showing the relative effects of photodynamic, hyperthermia, and combined photodynamic and hyperthermia treatment of a tumor.

The investigators found dramatic differences in treatment efficacy (see FIG. 8) for these protocols. In the mice treated with hyperthermia alone, only 5% showed no palpable tumors after one month. The mice administered photosensitizer and subjected to hyperthermia (but not PDT) all had palpable tumors, as did those subjected to hyperthermia followed by PDT. For those treated with PDT alone, about 10% showed no tumors after a month. However, where PDT was given first, *followed* by hyperthermia within 0.5 hour, about 45% of the mice were tumor free at month's end.

For treatment of this type of tumors in mice, PDT and heat was a potent combination. While different tumor systems will exhibit different levels of heat sensitivity, these data suggest that an implantable probe delivery system for PDT that also emits heat at the treatment site can be expected to have broader success than the more conventional fiber optic light wands now in development and use for PDT, which produce no intentional heating of the treatment site because an external light source is employed.

Exposure of tissue to extremely high temperatures during such treatments should, however, be avoided. Operating an LED or LD at high temperatures will reduce its efficiency, contribute to uneven light output from one LED (or LD) to the next, and potentially deteriorate bonds and materials within the light bar. Damage to normal tissue exposed to excessive temperatures can also occur. It is therefore desirable to control and monitor temperature rise and temperature gradients within the light bar structure and in the surrounding tissue.

Monitoring Tissue Temperature and Other Parameters

An elegant and simple method for monitoring temperature in and around the implantable probe uses the voltage-current characteristics of LEDs 120, for example, in implantable probe 40". The same technique is applicable to LDs used in place of LEDs 120. It is well-known that the forward and reverse conductances of pn-junction devices such as LEDs 120 are exponentially dependent on temperature. Hence, the simplest way to monitor probe temperature is to turn off the current flow to LEDs 120 for a time sufficient to allow the implantable probe 40" to reach equilibrium with the temperature of the surrounding tissue, and then to apply either a low forward or reverse bias voltage to the LED array, and measure current flow through the LEDs. This measurement can determine the temperature of the LED, if done while the LED (or LD) is emitting light or immediately after it ceases emitting light, before equilibrium is achieved; alternatively, if sufficient time has lapsed since the LED (or LD) has been de-energized, the measurement can determine the tissue temperature at the treatment site. Furthermore, this measurement can be accomplished without providing additional leads to the light bar, which is highly desirable, but requires either that implantable probe 40" (or other implantable probe) have leads that extend externally, or that the internal circuitry provide the necessary switching and temperature interrogation. In the latter case, it may be desirable to incorporate telemetry circuitry in the implantable probe that can relay the temperature information to external monitoring circuitry, which in turn, would adjust the LEDs' (or LDs') output directly or via the telemetry link.

By monitoring the temperature of the light bar, an optimal therapeutic regimen can be implemented, and if implementing hyperthermia in combination with PDT, the temperature of the surrounding tissue can also be monitored to avoid overheating and to maximize the efficacy of the combined treatment. The flow of electrical power (voltage, current, or both) applied to LEDs 120 can be regulated to either maintain an optimal tissue temperature and/or maximum light output. Current regulation can be performed completely internal to the human body if measurement and control circuitry is integral to the implanted probe, but a smaller and less costly alternative would place circuitry performing all or part of this function in a remote power source, eliminating the need for a custom integrated circuit to perform all or part of the necessary operations in the implantable probe. Because it is anticipated that some of the devices described here could be implanted and operated either continuously or periodically for extended periods of time, it would be preferable to employ control circuitry that regulates the on and off time of the LEDs, rather than the voltage or current. This approach increases overall system efficiency, since negligible power is then dissipated in controlling the temperature/light output.

Figure 20:
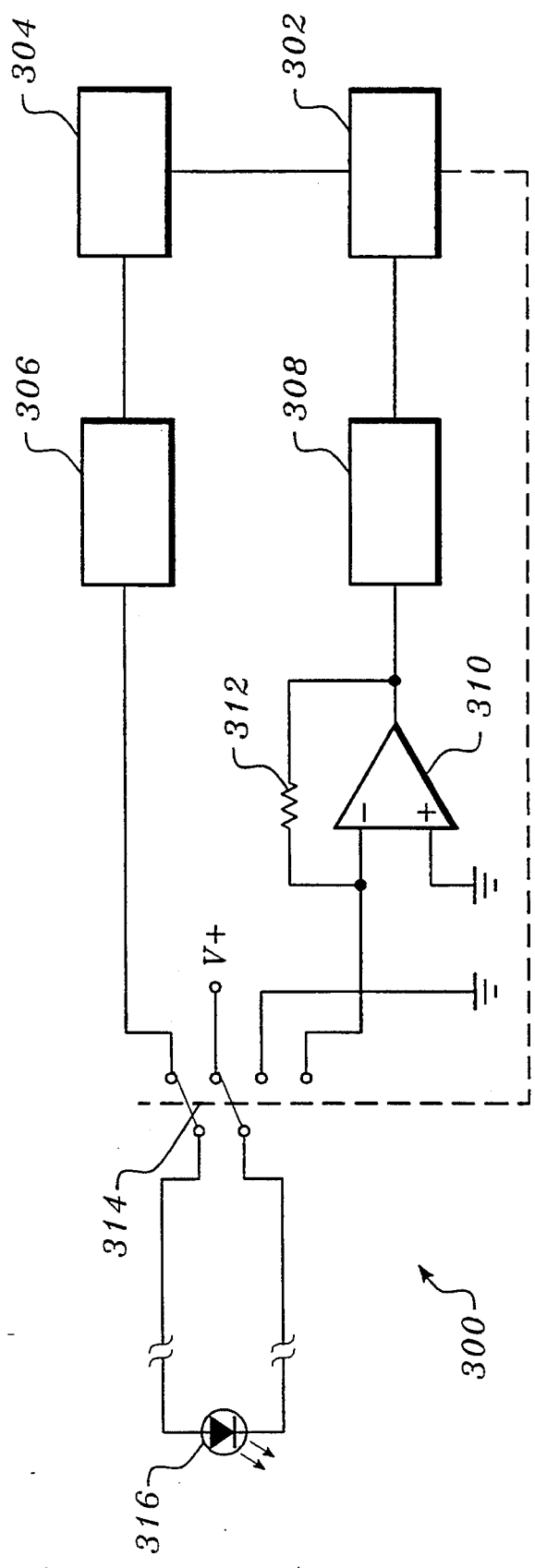
FIG. 20 is an electrical diagram of a light source control for use in the present invention.

Referring to FIG. 20, an exemplary control circuit 300 is illustrated for monitoring the voltage-current characteristics of an LED 316, which represents one or more LEDs 120 (or corresponding LDs) and is disposed at a treatment site. The monitoring determines the temperature of the LED and/or its immediate environment, e.g., the temperature of the surrounding tissue. Control circuit 300 includes a $\mu$-controller 302, a current source 306, a digital-to-analog converter (DAC)304, an analog-to-digital converter (ADC)308, an operational (OP) amp 310, and an electronic double-pole, double-throw (DPDT) switch 314. DPDT switch 314 is controlled by $\mu$-controller 302, as indicated by the dash line connecting the two devices in the Figure. When PDT is performed using LED 316 as the light source, DPDT switch 314 is in the position shown in the Figure, so that electrical current from current source 306 flows through the LED, at a level determined by the $\mu$-controller. The level of current provided by current source 306 is based on a digital signal produced by $\mu$-controller 302. Periodically, the $\mu$-controller causes DPDT switch to toggle to its other position, coupling the terminals of LED 316 to a relatively low forward bias voltage V+ and to the inverting input of OP amp 310. A resistor 312 determines the gain of OP amp 310, and thus, the output level of the OP amp, which corresponds to the forward voltage drop across LED 316. This forward voltage drop is a function of the temperature of the LED, and, after temperature equalization has occurred, a function of the temperature of the surrounding tissue at the treatment site. After waiting sufficiently long for LED 316 to substantially temperature equalize with its immediate environment, the analog output of OP amp 310 is digitized, and the resulting digital value is input to $\mu$-controller 302. Based on a predetermined acceptable voltage range corresponding to a predetermined acceptable temperature range for LED 316 (or its environment), $\mu$-controller 302 adjusts the digital output applied to DAC 304 to control the current, causing the current to increase or decrease as necessary to achieve a desired optimum light intensity or operating temperature for the PDT or combined PDT/Hyperthermia treatment. It should be noted, however, that instead of adjusting the current level applied to energize LED 316 to emit light, $\mu$-controller 302 can control the on and off time of the LED to maintain a desired temperature level, exposure time, or other parameter based on an appropriate sensor input signal indicative of the parameter.

Measurement of other probe parameters by the implantable probe is performed using either miniature electronic or optical sensors suitably mounted in the probe tip. Such a sensor (not shown) could be used to verify or control operation of the implantable probe and/or confirm treatment efficacy. Potentially valuable information that could be gathered by such sensors includes light output intensity, photoreactive agent tissue concentration, temperature (using a thermistor or other sensor instead of monitoring the LED voltage-current characteristic), $pO_2$, and pH.

Figure 9A:
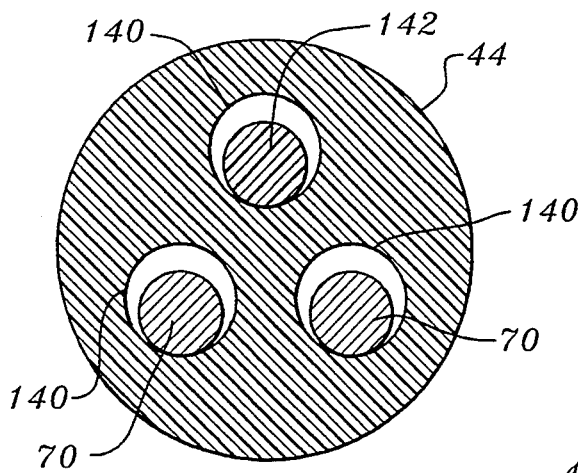
FIGS. 9A and 9B are cross-sectional views taken through a multi-lumen catheter, illustrating two configurations for an optical fiber coupled to an implantable probe.
Figure 9B:
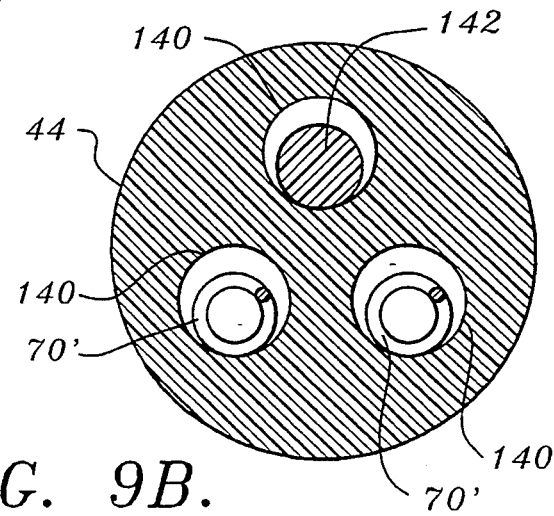

A traditional method for monitoring light output intensity would be to use a photodiode (not shown) placed adjacent LED array 54 of the implantable probe, in conjunction with a current-to-voltage operational amplifier circuit (not shown) in the implantable probe's LED drive module 56 or 56'. This approach would require one or two additional lead wires extending from the LED drive module to the tip of the implantable probe and is a viable option. However, it may be more advantageous to transfer a light signal back to the LED drive module using an optical fiber 142 placed within multi-lumen catheter 44, as in FIGS. 9A and 9B. This optical fiber would then interface with a photodiode/amplifier monitoring circuit (not shown) that is contained within LED drive module 56 or 56'. Note that power leads 70 extend through two of lumens 140, and optical fiber 142 extends through the third lumen 140 in FIG. 9A, while in FIG. 9B, helically coiled power leads 70' are shown; all other aspects of the flexible catheter embodiments shown in the these two Figures are the same.

Other Light Bar Geometries

The embodiments of the implantable probe heretofore discussed above have all been based on cylindrical geometries. It should be clear that the present invention can also be embodied in other shapes of an implantable probe. In particular, implantable probes with spherical or pancake shapes may be optimal for certain applications. FIGS. 10A and 10B show one such approach for an implantable probe 144, in which a single LED 148 is mounted in a plastic light-diffusing spheroid 152. Light-diffusing spheroid 152 is disposed on the distal end of a flexible catheter 44'. LED 148 is supported by a pedestal heat sink 146a, which extends into the distal end of the flexible catheter and is connected to one power lead 70. The other power lead 70 is coupled to LED 148 through a heat sink. 146b and a lead wire 150.

A spherical geometry for implantable probe 144 is optimal for producing a spherically uniform light radiation field, such as for use in providing PDT in the bladder or bastrointestinal (GI) tract. Uniform dispersion of light may be augmented by adding an optical dispersant to the polymer comprising the light-diffusing spheroid, or by texturing the surface of the spheroid. By increasing the size of the light-diffusing spheroid, additional LEDs facing in various radial directions (not shown) can be integrated into the design and a larger treatment area accessed with implantable probe 144.

A pancake-type, flexible implantable probe 160 is shown in FIGS. 11A and 11B that is designed for wrapping around a tumor, blood vessel, or other generally elongate treatment site (not shown). In this geometrical variant of the implantable probe, an LED array 166 is placed along a spine 168 of a light bar 162, which although not specifically shown for this embodiment, comprises a multi-layer laminate of the conductive foil and insulating layers like that discussed above in connection with implantable probe 40. The LEDs are shown mounted onto light bar 162 so as to dissipate heat and provide electrical connections. The other terminals of each of the LEDs are coupled by wires 170 to spine 168. The LEDs and light bar are encapsulated in a flexible light dispersing polymer 164, such as a silicone rubber or polyurethane. The surface of light bar 162 may be made reflective to maximize light output or textured to produce a desired light radiation pattern. The flexible light dispersive polymer used as the encapsulant may also have a textured or micro-ribbed surface (not shown) to generate a specific radiation pattern along the device's length or across its width when implantable probe 160 has assumed the curvature in which the PDT is provided.

PDT with Remote LED or Laser Light Source

For some applications of the present invention, it may be desirable to minimize thermal effects on surrounding tissue and place LEDs or laser diodes used as a light source at a remote location instead of on the light bar, by modifying implantable probes 40 or 40', for example, so that the light source is disposed in the LED drive modules (see FIGS. 2A or 2B), or outside the body, e.g., by including an optical fiber coupled to an external light source that supplies light conveyed to the implantable probe through the flexible catheter 44', in a modification (not shown) of implantable probe 40" (see FIG. 2C). In all these cases, it is desirable to use the largest diameter and highest numerical aperture optical fibers possible to convey the light into the implantable probe, thereby ensuring that the loss in efficiency associated with propagating the light through the optical fiber from the source is kept to a minimum.

The clinician, however, has a somewhat different perspective. He or she would like a flexible catheter/implantable probe that has a comparatively small cross section, can be stiffened for insertion, can be monitored by using fluoroscopy or other imaging modality (to determine its position inside the patient's body), and which allows adjustment in the length inserted into the treatment site. Flexibility of the catheter during the treatment period is desirable, as is the option of infusing photoreactive agent or medication from time-to-time through the flexible catheter, or withdrawing fluid samples from the body through the flexible catheter, for analysis.

Figure 12A:
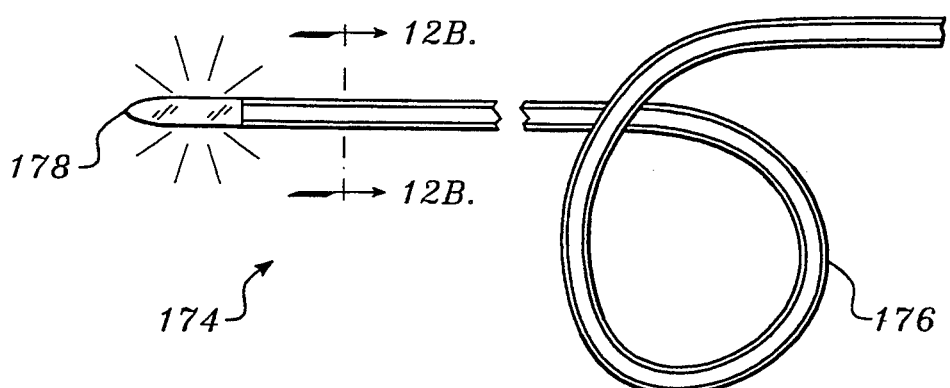
FIGS. 12A, 12B, and 12C are a plan view, a cross-sectional view (taken along section lines 12B—12B), and an isometric exploded view, respectively, of yet another embodiment for an implantable probe.
Figure 12B:
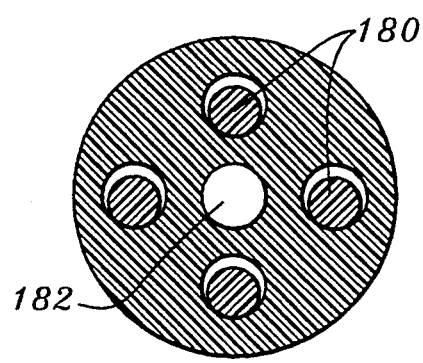
Figure 12C:
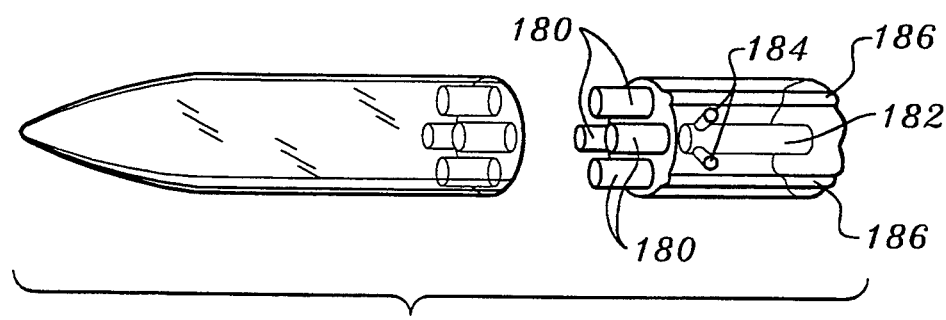

An implantable probe 174, shown in FIGS. 12A through 12C accomplishes these goals. The strategy employed for this embodiment is to use a multi-lumen flexible catheter 176, which incorporates a plurality of high numerical aperture plastic or glass optical fibers 180 clustered around an open central lumen 182. The central lumen is used during placement of flexible catheter 176 and implantable probe 174, and for photoreactive agent delivery.

During placement of the flexible catheter, a guide wire (not shown) is inserted in central lumen 182. This wire is used to direct and locate a light distribution tip 178 to the desired treatment site. A radio-opaque substance or magnetic resonance (MR) visible substance can be added to flexible catheter 176 to aid visualization of the implantable probe during the placement process. After light distribution tip 178 has been set in place, the wire is removed and the rear of the flexible catheter is connected to an external source of light produced, for example, by an array of LEDs or laser diodes. An example of such an external light source is disclosed below.

Each optical fiber 180 occupies a single lumen and is sealed only at the ends of the flexible catheter. i.e., the optical fibers are not bonded to the interior surface of the lumens along most of the length of flexible catheter 176. The use of multiple end-sealed optical fibers 180 allows flexible catheter 176 to be much more flexible than if the optical fibers were bonded into it all along it's length. Light distribution tip 178 provides an even distribution of light emitted by implantable probe 174, by diffusing the light emitted from the distal ends of optical fibers 180. Each optical fiber is adhesively bonded or heat-fused into light distribution tip 178. The outer surface of the distal ends of optical fibers 180 is textured to provide uniform light distribution and coupling into the light distribution tip. This approach can, of course, be used for connection to other light distribution tips having other geometric shapes such as spherical, or pancake shapes, like the shape of implantable probes 144 and 160 in FIGS. 10A and 11A, respectively.

Alternatively, the light distribution tip can be extruded in the shape of a cylinder (not shown) with an array of axial through-holes that match optical fibers 180 in number and size. In this case, the optical cladding on the individual optical fibers is removed and the optical fibers are threaded through the entire length of the light distribution tip. By adjusting the surface texture of the fibers, the adhesive, and the extruded shape of the light distribution tip, a highly uniform light radiation field can be produced by implantable probe 174.

As noted above, lumen 182 and ports 184 that extend radially outward from the lumen provide a fluid path for perfusing photoreactive agent into the treatment site from an external source during the PDT.

Figure 12D:
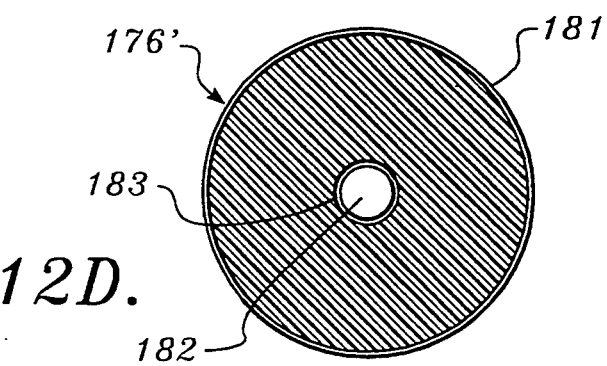
FIG. 12D is a cross-section view, analogous to the cross-sectional view of FIG. 12B, of a modified catheter that conveys light through the material comprising the catheter, to the implantable probe.

If a catheter 176', as shown in FIG. 12D, is manufactured of a highly transparent material such as polymethylmethacrylate (PMMA) or silicone rubber, it may be possible to eliminate use of a discrete optical fiber array within the catheter by using the catheter itself as a light guide. In that event, an exterior surface of catheter 176' would be formed with very smooth contours and would be coated with a thin layer of a material 181 or cladding film having a refractive index lower than that of the catheter body, to ensure that light is trapped within the catheter as it propagates from the proximal to the distal end of the catheter. Light distribution to the treatment site can be effected at the distal end of the catheter by removing the coating of material 181 over the desired output region of the catheter, and/or by abrasively roughening the exterior surface of the light guiding catheter. Discrete light distribution tips 178 of diverse shape may also be attached using transparent adhesives.

Incorporation of and use of a center lumen 182 for wire guided placement would be possible with no special interior surface,' preparation. Center lumen 182 or other interior lumens could also be used for the perfusion of photoreactive agents, the placement of monitoring optical fibers, or as a conduit for electronic sensor leads if a layer 183 of the low refractive index material 181 were coated onto the surface of each such lumen. If catheter 176' is formed of PMMA, then material 181, and layer 183 can comprise low index silicones or fluoridated hydrocarbons.

Figure 13A:
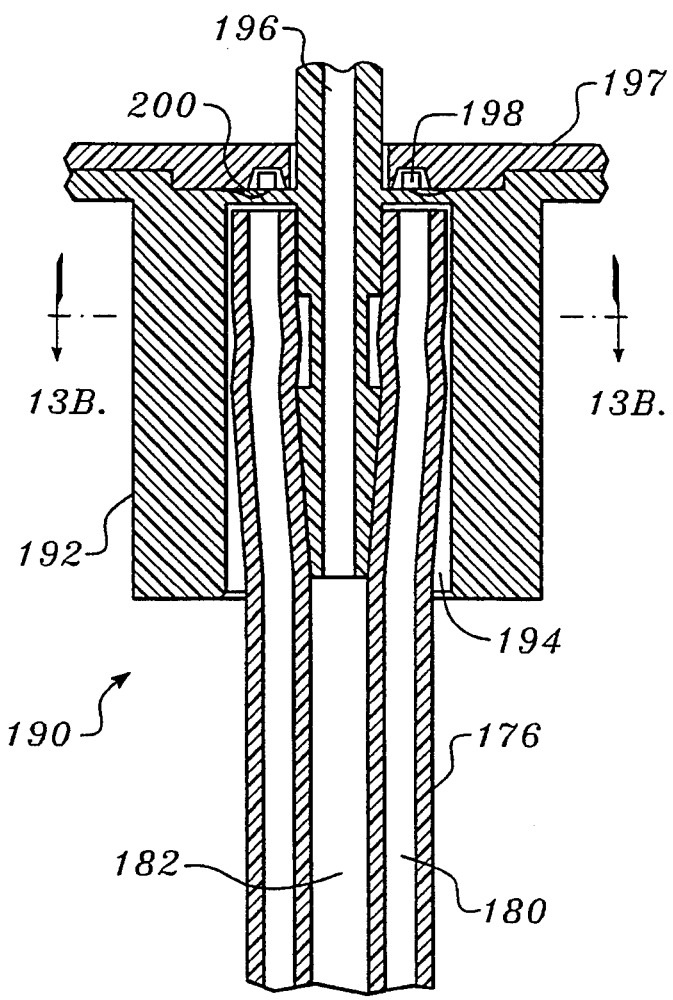
FIGS. 13A and 13B are a side cross-sectional view and a transverse cross-sectional view (taken along section lines 13A—13A) of an array of light sources and an optical fiber array fitted to the light sources.
Figure 13B:
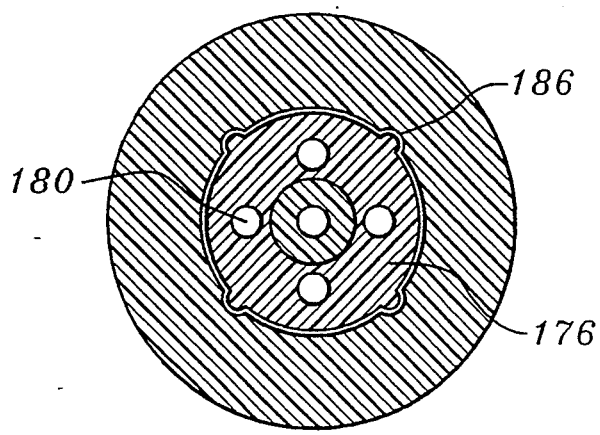

The physical connection between the flexible catheter and the source of light must provide efficient transfer of light from an LED or LD array within the source to light guiding catheter 176' or to optical fibers 180 in flexible catheter 176. An exemplary design for a light source 190 and a coupling 192 used with flexible catheter 176 and optical fibers 180 is shown in FIGS. 13A and 13B. Flexible catheter 176 has been molded to include four small axial external ribs 186 that extend longitudinally, provided at least adjacent its proximal end. These fibs slide into and mate with corresponding longitudinally extending internal grooves 194 in coupling 192, indexing the flexible catheter in a rotational sense, while an on-axis hose barb 196 locates flexible catheter 176 in a coaxial sense. Directly opposite from the proximal butt ends of optical fibers 180, in a base 197, are four LEDs 198 (only two are shown in the Figure) supplying each optical fiber with light. The small intervening gap between the LEDs and the butt end of the corresponding optical fibers is filled with a transparent index matching gel (not specifically referenced or shown in the Figure), which increases optical coupling efficiency and shields the joint from body fluids. Since most LEDs are approximately 200–300 microns in diameter, conventional plastic optical fibers of 500–1000 microns in diameter can be aligned to the LEDs with good coupling efficiency. Also, the use of a plastic optical fiber reduces the cost of fiber end preparation, which can be substantial for a conventional quartz-based telecommunications fiber. If catheter 176' is the light guide (instead of the optical fibers), its rotational alignment is unnecessary and external fibs 186 are not needed.

In either case, with coupler 192 shown in FIGS. 13A and 13B used for coupling the LEDs or (LDs) to the light guide(s), it may be possible for the user to cleave the flexible catheter to an arbitrary length (at the proximal end) without compromising the light delivery efficiency. This capability reduces the number of catheter lengths that must be manufactured to treat tumors at different depths.

This trimmable capability would be difficult to implement with glass optical fibers. In addition to the problem of polishing the butt ends of glass optical fibers, glass optical fibers are much stiffer than plastic and it would not be possible to use as large diameter glass optical fibers without a severe handling flexibility penalty. Also, glass optical fibers in larger diameters are typically limited to about a 0.38 numerical aperture, whereas plastic optical fibers can be obtained with numerical apertures as high as 0.60. This specification translates into approximately a factor of 2.5 times higher light throughput for a plastic optical fiber, compared to a glass optical fiber of the same diameter. Plastic optical fibers also more closely match the thermal expansion properties of a plastic flexible catheter.

The only potential negatives associated with the use of plastic optical fibers 180 or transparent catheter 176' are higher loss (about 5-10% per meter of length) and a tendency on the part of some polymers used for plastic optical fibers to lose transparency after long-term immersion in water (or body fluids). Most flexible catheters that would be used in this application are comparatively short and higher loss is not a significant problem. The effects of long-term water immersion on different plastic optical fiber materials is not well understood. Haze from water absorption is typically slow to develop and may not be an issue for implantation times of up to several days. Various polymer coatings on the plastic optical fiber 180 may also retard this hazing process.

While implantable probe 174 shown in FIGS. 12A and 12B can be used with an internal power source, connection with the exterior world could allow other clinical procedures, such as fluid injection and/or fluid sample withdrawal to be performed through the central lumen in flexible catheter 176 or in light guiding catheter 176'. Only relatively minor changes are needed to increase system functionality in this embodiment of the subject PDT apparatus.

If the light source is to be external for use with implantable probe 174, then it may be more practical to use commercial pre-packaged low-power laser diodes (not bare chips) in external light source 190 in place of the LEDs. Pre-packaged, low power solid-state laser diodes, typically developing 1-20 mW, are much less expensive than the high powered laser diodes being developed for the prior art PDT systems—their principal applications are as light sources for use in connection with bar code readers and optical discs. While the cost of even a pre-packaged low power laser diode is approximately a factor of 10 to 50 times greater than an LED, it may be possible in this particular modality to transfer more of a laser diode's light to an optical fiber, since the laser diode approximates a point source and the LED is a more diffuse light emitter.

A new generation of laser diode arrays is being developed that are of particular interest for incorporation into internal or external light sources for PDT systems in accordance with the present invention. These laser diode arrays employ vertical cavity surface-emitting lasers (VCSELs). For use as background information and therefore not shown in the drawings, it should be noted that most previous laser diodes have been so-called edge emitters, which emit light along the axis of a channel made in the semiconductor wafer's surface. To emit light, the wafer on which the laser diode is formed must be cleaved perpendicular to the channel and the resulting chip mounted at 90° on a heat sink.

In contrast to edge emitting laser diodes, VCSELs are made using somewhat similar planiar processes, but light emission is inherently perpendicular to the wafer's surface, allowing arbitrary one or two-dimensional arrays of light sources to be fabricated on a wafer substrate and providing inherent heat sinking to the wafer substrate. Output powers of 2-3 mW per array element have been achieved, and $32 \times 32$ arrays have been developed in prototype. Consequently, an array of laser diodes can be made for a cost that is not much more than that of a single VCSEL. A package including a VCSEL array enables cost-effective PDT designs to be implemented, wherein individual laser diodes can be selectively turned on or off, or, modulated in intensity to provide an optimum light pattern at the treatment site. Such options are not possible or at least, not practical, with high power output laser devices, or with an array of packaged low-power laser diodes. For the $32 \times 32$ array noted above, the cost of discrete packaged light emitting devices would be prohibitive.

While a typical edge emitter laser diode might have a 19° by 60° emission pattern, a typical VCSEL diode has an emitting area less than 10 microns in diameter and a circular beam divergence of 7°-8°. This characteristic allows for much easier coupling of VCSELs to optical fibers.

Figure 14:
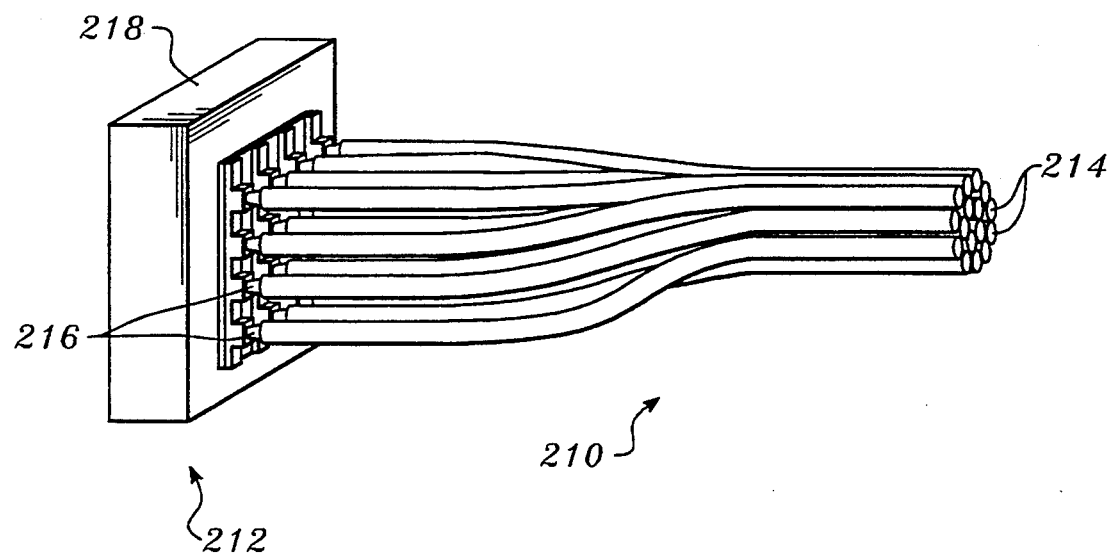
FIG. 14 is an isometric view of another embodiment of an array of light source coupled to a plurality of optical fibers.

FIG. 14 shows an external VCSEL light source 212 for use with the PDT system of the present invention. In external VCSEL light source 212, a plurality of optical fibers 214 comprising a bundle 210 are coupled to the regularly-spaced narrow emission beams emitted by a corresponding plurality of VCSEL diodes 216, which are mounted on a base 218, with very good overall coupling efficiency. A molded assemblage of focusing lenses (not shown) can optionally be used to concentrate the emitted light into even smaller optical fibers, at some increase in cost and complexity. By using smaller, more flexible optical fibers 214, improvements in catheter flexibility and/or light delivery efficiency can be achieved.

Figure 15A:
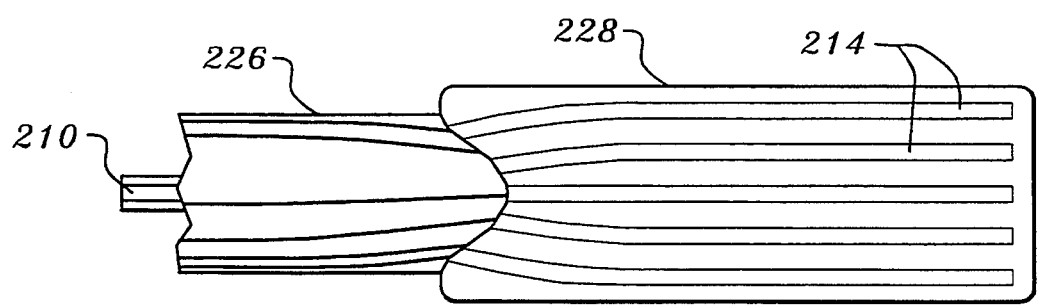
FIGS. 15A and 15B are a side view and end view, respectively, of another embodiment of an implantable probe coupled to a plurality of optical fibers.
Figure 15B:
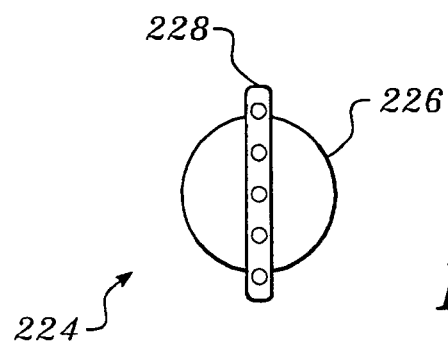

External VCSEL light source 212 also allows a flat or pancake-type implantable probe 224 that is sufficiently flexible to wrap-around a treatment site to be made, wherein the light-emitting distal portions of optical fibers 214 comprising bundle 210 are spread apart in probe 224, as shown in FIGS. 15A and 15B. In these Figures, the individual optical fibers, which extend through a flexible catheter 226, have been molded into a flat strip 228 of a transparent polymer. The arrangement of optical fibers in probe 224 can be varied to produce a wide variety of light emission patterns (as can LED arrays 54 and 54' in the other embodiments of the implantable probe previously disclosed above).

Figures 21A, 21B:
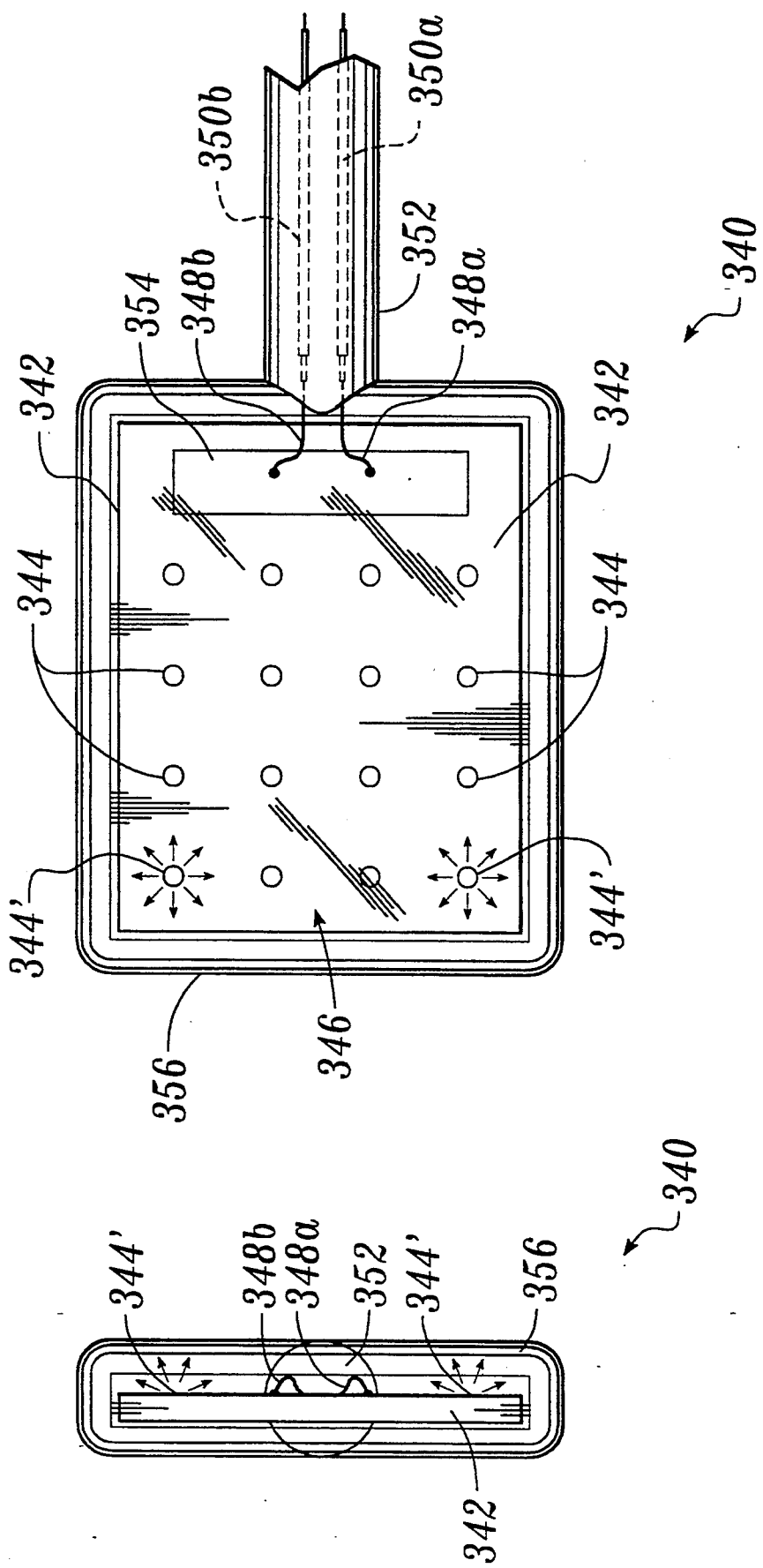
FIGS. 21A and 21B are a plan view and an end elevational view of another embodiment of an implantable probe that includes an array of VCSELs.

A VCSEL light source could also be implanted in a patient's body for long term therapeutic PDT. An example of such an implantable probe 340, is shown in FIGS. 21A and 21B. Implantable probe 340 comprises a generally quadrilateral-shaped, planar substrate 342 on which are mounted sixteen VCSELs 344, spaced apart to form an array 346. Electrical power to energize VCSELs 344 is supplied through conductors 348a and 348b, which extend through corresponding lumens 350a and 350b in a catheter 352. The distal end of catheter 352 supports implantable probe 340 and carries the conductors to a power source (is not shown), which is disposed apart from the treatment site, either outside the patient's body, or at a different location within the body than the treatment site. Conductors 348a and 348b are electrically connected to an embedded multiplexing (or alternatively, modulating) circuit 354, which selectively energizes any of the sixteen VCSELs 344 (e.g., VCSELs 344') to provide a desired geometrical patttern of light on the treatment site. By multiplexing the VCSELs so that less than all sixteen are energized at a time, the instantaneous current that must be supplied by the power source is less than if all of the VCSELs in array 346 were energized simultaneously. Alternatively, if the embedded modulator circuit is provided on substrate 342, instead of the embedded multiplexing circuit, the intensity of light emitted by VCSELs 344 can be selectively controlled. In either case, the embedded multiplexing (or modulating) circuit 354 could be controlled using pulses transmitted over conductors 348a and 348b, or in response to electromagnetically coupled signals from outside of the patient's body, under an operator's control. Details of such circuits are well known to those of ordinary skill in the art and need not be disclosed herein.

VCSELs 344 and substrate 342 on implanttable probe 340 are encapsulated in a plastic housing 356 or with a material selected for its physiological compatibility, optical properties, and thermal conductivity. The planar shape of substrate 342 enables the housing or encapsulant to be relatively thin so that the implantable probe can readily be placed at diverse locations, either near or spaced apart from the treatment site.

Multi-Function PDT Systems

Figure 16A:
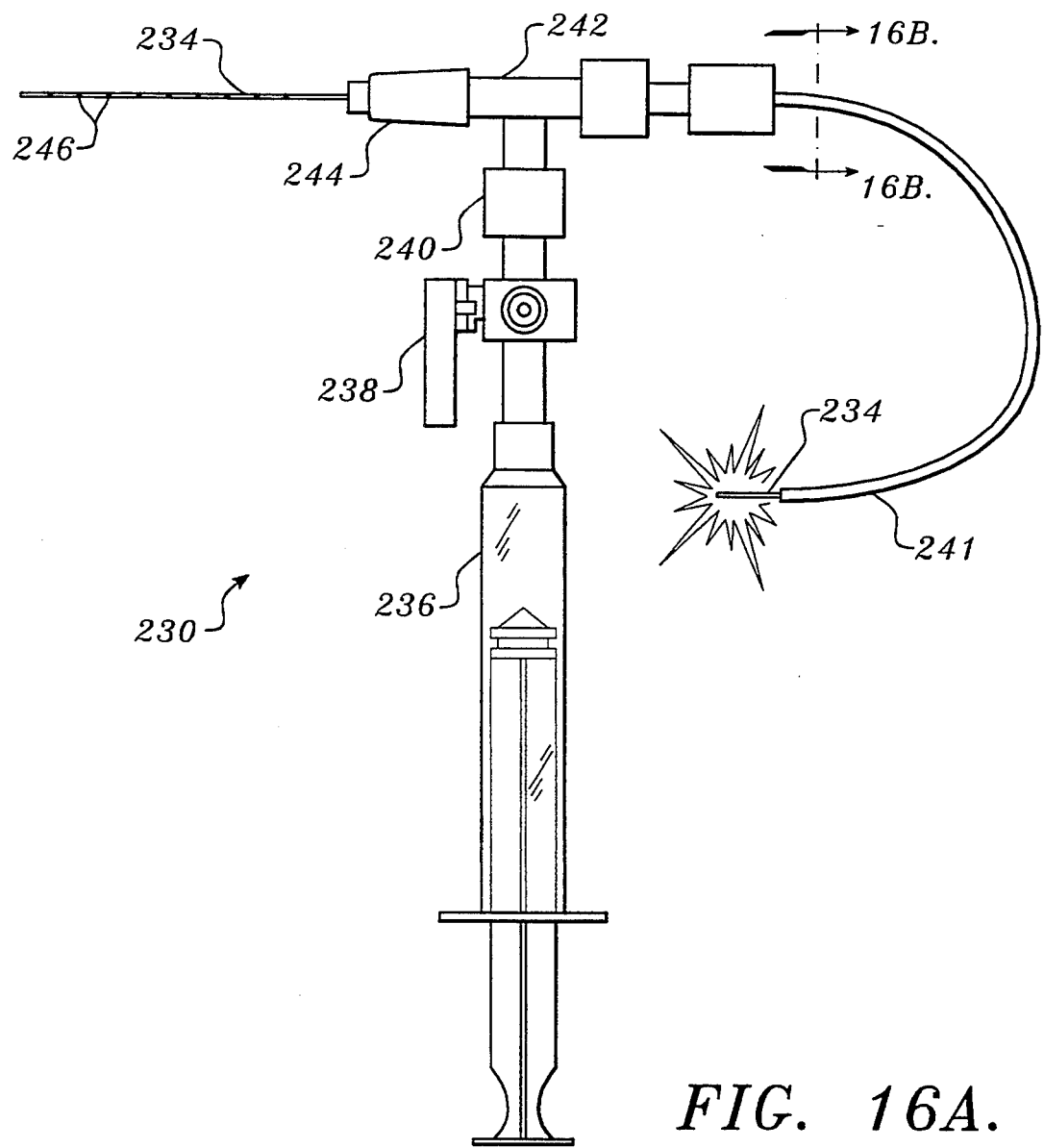
FIGS. 16A and 16B are an elevational view and a cross-sectional view (taken along section lines 16B—16B), respectively, of apparatus for simultaneously infusing a fluid and delivering light to an implantable probe from an external source.
Figure 16B:
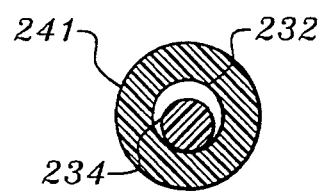
Figure 17:
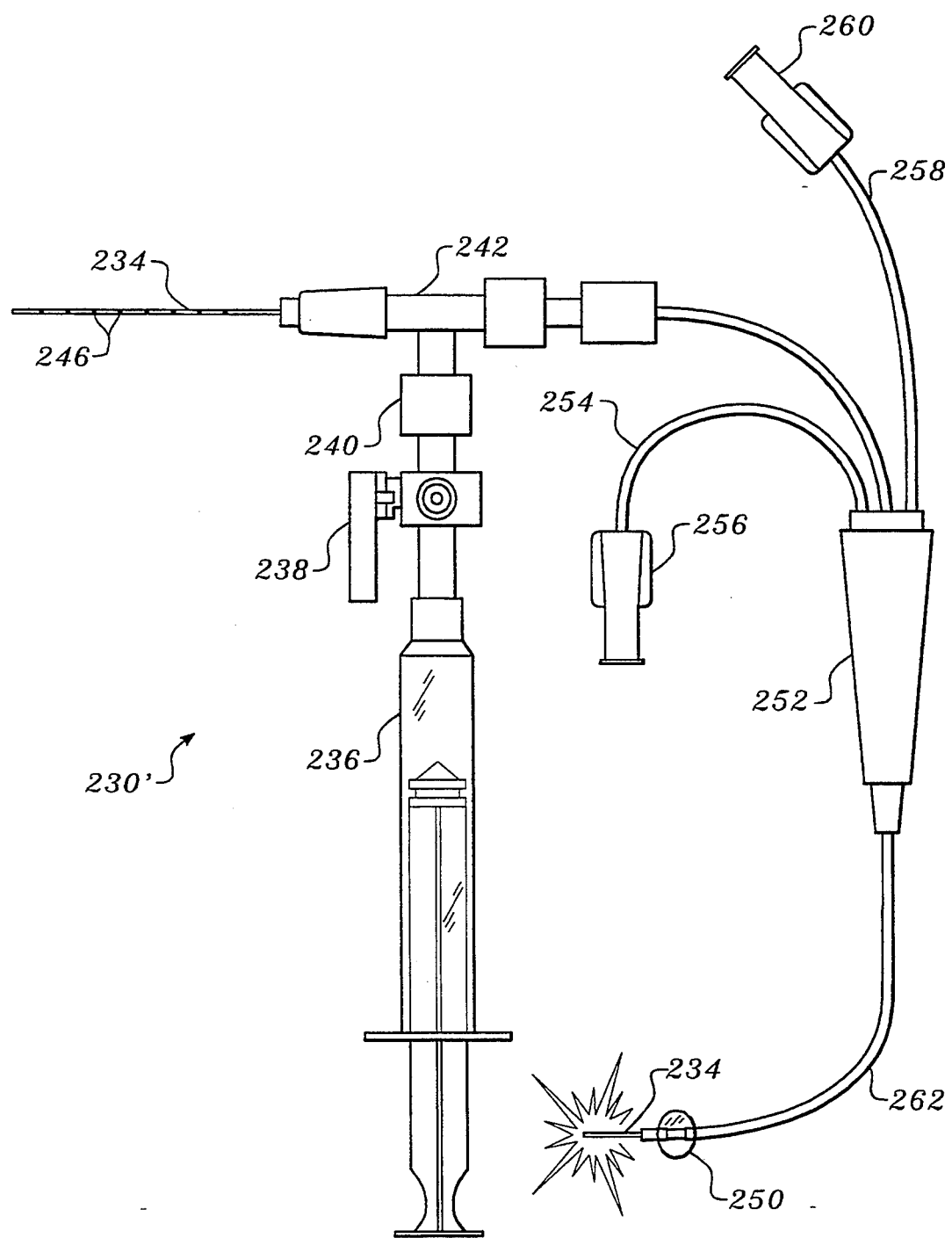
FIG. 17 is an elevational view of apparatus for infusing a fluid, delivering light, and inflating a balloon on a catheter that is also used to provide PDT.
Figure 18:
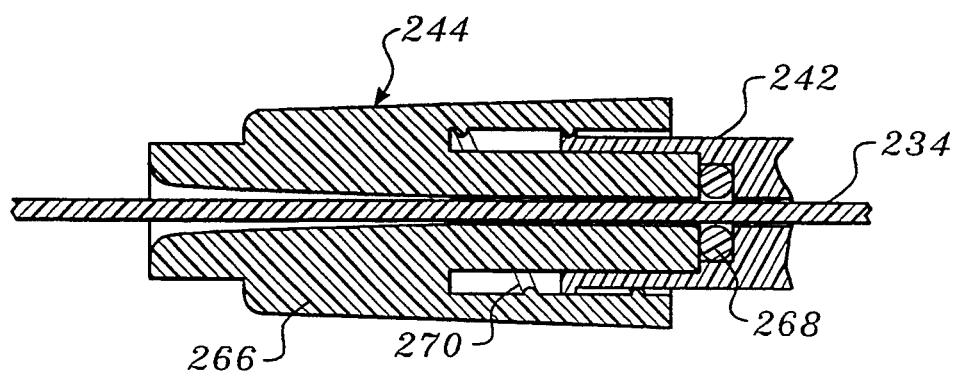
FIG. 18 is a cross-sectional view of a Luer lock nut for sealing around an optical fiber.

A single optical fiber, light source PDT system can be made that is very versatile in providing additional functions. FIGS. 16A, 16B, and 17 show two PDT systems that not only allow the use of a guide wire for flexible catheter placement prior to the onset of PDT, but also permit infusion of photoreactive agent or medication during the PDT. A PDT system 230 (the external laser diode or LED light source not being shown) in FIGS. 16A and 16B includes a flexible catheter 241 through which a single optical fiber 234 extends in an annular flow channel 232. PDT system 230 includes a syringe 236 that is coupled to a two-way valve 238. One port of the two-way valve is connected through a conventional Luer fitting 240 to a T-fitting 242, through which optical fiber 234 extends. The T-fitting includes a seal lock nut 244 that seals around the optical fiber, locking it in place at a particular point of advancement through flexible catheter 241, and preventing any fluid leakage around the optical fiber. A plurality of position markers 246 are provided on optical fiber 234 to assist in determining the degree to which the distal end of the optical fiber has been advanced beyond the distal end of the flexible catheter, inside the patient's body. Use of seal lock nut 244 also allows the flexible catheter to be cut to length at the distal end and allows the user to remove or replace optical fiber 234, as appropriate. In addition, a guide wire (not shown) can be threaded through the T-fitting, and temporarily locked in place, for flexible catheter placement inside the patient's body.

Fluid such as a photoreactive agent can be injected with syringe 236 through annular flow channel 232, to exit at the distal end of the flexible catheter, thereby providing, for example, subsequent perfusion of the photoreactive agent at the treatment site after optical fiber 234 is properly positioned before and during PDT. Alternatively, blood or other bodily fluid samples can be withdrawn from the treatment site at the distal end of flexible catheter 241 through annular flow channel 232. Two-way valve 238 provides the user the capability to either inject fluid or withdraw fluid with the syringe, depending upon the position of the two-way valve.

FIG. 17 shows a 3-lumen balloon-type catheter 252 with a distal balloon 250 set up for use with a PDT system 230'. A line 254 couples a proximal lumen hub 256 in fluid communication with one of the lumens in flexible catheter 262, and a line 258 couples a balloon inflating valve 260 in fluid communication with another lumen so that distal balloon 250 can be inflated with pressurized fluid. All other components of PDT system 230', except flexible catheter 241, are identical to PDT system 230. By inflating distal balloon 250 with fluid under pressure provided through balloon inflating valve 260, flow of a fluid in a vessel of the patient's vascular system can be interrupted during the PDT treatment. Alternatively, the distal balloon can be used for angioplasty procedures that are carried out in connection with PDT.

Exterior Use of Implantable Probes

The implantable probes disclosed above are primarily intended for use inside the body, where a skin penetration, perhaps requiring minor surgery, is necessary to introduce and position the implantable probe at the treatment site. They could in certain circumstances alternatively be applied to provide PDT for external surfaces of the patient' body. Implantable probes 160 (FIGS. 11A and 11B) and 224 (FIGS. 15A and 15B) are particularly adaptable for such externally applied PDT.

Figure 19A:
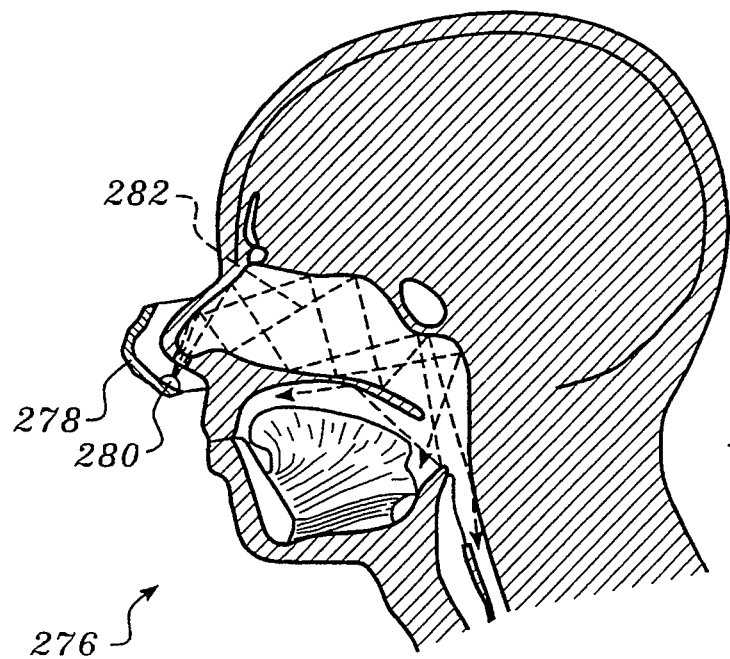
FIGS. 19A and 19B are schematic views from the side and from of a human skull, illustrating the technique for delivering PDT to sinus cavities within the skull.
Figure 19B:
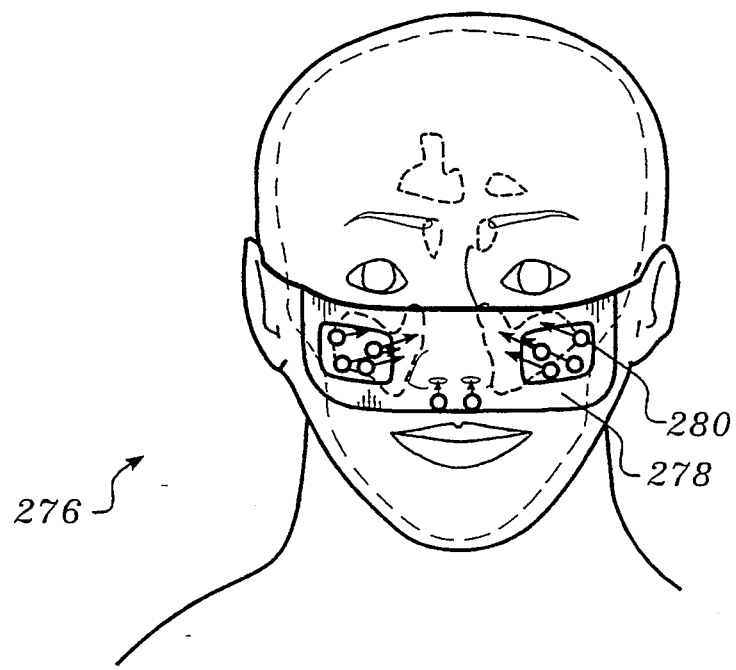

A particularly interesting and challenging application for PDT is in curing or alleviating complications of the common cold. It may be possible to cure or reduce the severity and length of the common cold with the topical application of a spray containing an appropriate photoreactive agent to the nose, mouth, and throat, followed by an overnight dose of light, as shown in FIGS. 19A and 19B. This PDT system incorporates a partial face-coveting mask plate 278 with two embedded arrays of LEDs 280 and two discrete LEDs 280. The array of LEDs 280 are arranged on plate 278 to illuminate the skin over the maxillary and ethmoidal sinuses, while the discrete LEDs are arranged to inject light through each nostrils vestibule 282 and to internally illuminate the exposed interior sinus and nasal cavity surfaces.

This PDT would not be a palliative treatment that masks symptoms or alters the bodies' natural reactions. Rather, the patient would function better because the viral load had been reduced in treated areas, inside the throat, nasal, and sinus cavities of a patient's skull that are accessible by direct and reflected light from the LEDs, as shown in the Figure.

Considering the possible operating mechanisms of PDT, it may be difficult for viruses to establish a resistance to this treatment. Also, since the levels of light that show efficacy are not likely to harm normal eyes, the photoreactive agents are generally considered innocuous, and operating voltages used to energize LEDs 280 are typically less than 2.0 volts, it may eventually be possible to sell this treatment over-the-counter.

An open question at this time is, of course, the relative effect of PDT on the virus versus the infected tissue or mucous membranes. A difficulty with applying PDT techniques that activate singlet oxygen is that the oxygen generated may kill or otherwise disrupt normal cells, and show little therapeutic selectivity. However, since cold and flu viruses possess unique structures and have a unique interaction with the body, it may be possible to produce or identify a photoreactive agent that specifically targets the viral pathogen. Treatment of such pathogens may also involve the use of longer wavelength light, which is ineffective in producing singlet oxygen, yet is capable of interacting with one or more photoactive agents to produce antiviral activity via a non-cytotoxic reaction pathway.

The LEDs/LDs used for light injection into the nasal cavity could be equipped with lenses that generate an image of the LED/LD point source at a focal point approximately half-way through the nasal vestibule. This focusing of the light would provide a comparatively narrow beam to gain entry into the nose, and a rapid divergence of the light once inside, to maximize light dispersion to all surfaces. Studies of light dispersal in life-size model heads indicate that the various complex surfaces within the nose should assist significantly in light scattering and that some light should even reach the pharyngeal surfaces in the throat.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for photodynamic treatment at an internal, in vivo treatment site, to cause a desired therapeutic change, comprising the steps of:
   (a) applying a photoreactive agent to the internal, in vivo treatment site, said photoreactive agent being selected for one or more characteristic wavelengths or wavebands of light absorption;
   (b) positioning a light source that directly generates light internally within a patient's body, said light source being transcutaneously delivered to the in vivo treatment site and left implanted within the patient's body during the photodynamic treatment, the light emitted by the light source having one or more emission wavelengths or wavebands substantially equal to a wavelength or waveband of absorption of the photoreactive agent; and
   (c) administering the light emitted from the light source to the internal, in vivo treatment site, said light being absorbed by the photoreactive agent, which then causes the desired therapeutic change at the treatment site.

2. The method of claim 1, wherein the step of positioning the light source comprises the steps of:
   (a) providing a catheter having; a distal end and a proximal end, said light source being disposed at the distal end of the catheter;
   (b) moving the catheter and the light source into a patient's body; and
   (c) positioning the catheter so that its distal end and the light source are disposed proximate to the internal, in vivo treatment site.

3. The method of claim 2, wherein said catheter includes at least one lumen that extends generally between the proximal and distal ends of the catheter, further comprising the step of coupling a supply of the photoreactive agent in fluid communication with said at least one lumen, at the proximate end of the catheter; wherein the step of applying comprises the step of causing the photoreactive agent to flow through said at least one lumen so that it perfuses the internal, in vivo treatment site at the distal end of the catheter.

4. The method of claim 1, wherein the step of positioning the light source comprises the steps of:
   (a) invasively disposing the light source proximate to the internal, in vivo treatment site inside a patient's body; and
   (b) leaving said light source in the patient's body while administering light to the treatment site, until the desired therapeutic change has occurred.

5. The method of claim 4, wherein the step of invasively disposing said light source, comprises the steps of:
   (a) causing a penetration of the patient's body to access the internal, in vivo treatment site; and
   (b) closing said penetration, leaving said light source implanted within the patient's body.

6. The method of claim 4, wherein the step of providing the light source comprises the step of providing at least one light emitting diode; and wherein the step of invasively disposing said light source comprises the step of disposing said at least one light emitting diode proximate to the internal, in vivo treatment site, to illuminate the treatment site with light emitted by said at least one light emitting diode.

7. The method of claim 4, wherein the step of providing the light source comprises the step of providing at least one laser diode; and wherein the step of invasively disposing said light source comprises the step of disposing said at least one laser diode proximate to the internal, in vivo treatment site, to illuminate the treatment site with light emitted by said at least one laser diode.

8. The method of claim 2, wherein said catheter includes at least one lumen that extends generally between the proximal and distal ends of the catheter, further comprising the steps of:
   (a) providing an external power supply and electrical conductors connected thereto; and
   (b) supplying electrical current from the external power supply through the electrical conductors to energize the light source, said electrical conductors extending through the lumen from the external power supply to the light source.

9. The method of claim 1, wherein said light source comprises at least one light emitting diode, further comprising the step of periodically monitoring a temperature of the internal, in vivo treatment site by determining a voltage-current characteristic of said at least one light emitting diode.

10. The method of claim 1, wherein :said light source comprises at least one laser diode, further comprising the step of periodically monitoring a temperature of the internal, in vivo treatment site by determining a voltage-current characteristic of said at least one laser diode.

11. The method of claim 1, further comprising the steps of:
   (a) providing an external source of electrical power; and (b) electromagnetically coupling the external source of electrical power to the light source to provide an electrical current used to energize the light source.

12. The method of claim 1, further comprising the step of disposing a self-contained power source with the light source within the patient's body, to provide an electrical current to energize said light source.

13. The method of claim 1, further comprising the step of heating the treatment site to improve an efficacy of the photodynamic treatment.

14. The method of claim 13, wherein the step of heating comprises the step of using waste heat from the light source that is disposed proximate to the internal, in vivo treatment site.

15. The method of claim 1, further comprising the step of monitoring a physiological parameter at the internal, in vivo treatment site to determine an efficacy of the photodynamic treatment.

16. The method of claim 1, further comprising the step of periodically infusing the photoreactive agent into the internal, in vivo treatment site.

17. The method of claim 16, wherein the step of periodically infusing comprises the step of infusing the photoreactive agent through a catheter from at least one external reservoir.

18. The method of claim 16, wherein the step of periodically infusing comprises the step of infusing the photoreactive agent from at least one reservoir that is disposed with the source light, inside the patient's body.

19. The method of claim 1, wherein the light source comprises a plurality of light sources, and wherein the step of administering the light comprises the step of sequentially energizing selected ones of the plurality of light sources to illuminate different portions of the internal, in vivo treatment site, as said selected ones of the plurality of light sources emit light.

20. Apparatus for administering photodynamic treatment at an internal, in vivo treatment site, to cause a desired therapeutic change, comprising:
(a) a light source having at least one characteristic emission wavelength or waveband suitable for the photodynamic treatment;
(b) a supporting structure for said light source, said supporting structure being adapted for invasive disposition within a patient's body, to support the light source proximate to said internal, in vivo treatment site, shaped to administer light generated by the light source directly to said treatment site from the light source without conveying the light over an optical fiber from a point external to the patient's body, and adapted to be inserted transcutaneously and implanted during the photodynamic treatment, allowing said light source to be selectively energized to directly irradiate the internal, in vivo treatment site with said light, to cause the desired therapeutic change at the treatment site, heat produced by the light source being absorbed by the treatment site to improve the efficacy of the photodynamic treatment; and
(c) a power supply that provides an electrical current to energize the light source.

21. The apparatus of claim 20, wherein the light source comprises at least one light emitting diode.

22. The apparatus of claim 20, wherein the light source comprises at least one laser diode.

23. The apparatus of claim 20, wherein the power supply comprises an infrared light source and an infrared detector that converts infrared light into the electrical current used to energize the light source.

24. The apparatus of claim 23, wherein said infrared light source is adapted to produce infrared light directed onto a patient's body, said infrared light penetrating the patient's body to reach the infrared detector, which is adapted to be disposed inside the patient's body.

25. The apparatus of claim 20, wherein the supporting structure comprises a catheter having a distal end adapted to be disposed at the internal, in vivo treatment site, and a proximal end that remains outside a patient's body.

26. The apparatus of claim 25, wherein the catheter includes at least one lumen extending generally through the catheter from its proximal end to its distal end, further comprising a supply of the photoreactive agent that is connected in fluid communication with said at least one lumen to perfuse the internal, in vivo treatment site, and is disposed outside of the patient's body, said photoreactive agent flowing through said at least one lumen from the supply and exiting said at least one lumen at the distal end of the catheter.

27. The apparatus of claim 25, wherein the catheter includes at least one lumen extending through the catheter, generally from its proximal to its distal end, the proximal end of the catheter remaining outside of the patient's body, and wherein the power supply is external to the patient's body, further comprising electrical conductors coupled electrically to the power supply that extend through said at least one lumen in the catheter to the light source, the electrical conductors conveying the electrical current from the power supply to energize the light source.

28. The apparatus of claim 25, further comprising a sensor that is disposed at the distal end of the catheter and a corresponding monitoring instrument, said sensor being coupled to the monitoring instrument, which is used to determine an efficacy of the photodynamic treatment at the treatment site by monitoring a physiological parameter indicative of the efficacy.

29. The apparatus of claim 25, wherein the supporting structure further comprises a probe disposed at the distal end of the catheter, said probe including a substrate upon which the light source is mounted.

30. The apparatus of claim 29, wherein the substrate is an insulator and wherein the supporting structure further includes first and second conductors, said first and second conductors electrically coupling said power supply to the light source.

31. The apparatus of claim 30, wherein said probe has a longitudinal axis, and said substrate is elongate and extends within said probe in a direction generally parallel to said longitudinal axis, said light source comprising a plurality of light emitting devices arranged in spaced-apart array along said substrate.

32. The apparatus of claim 31, wherein the plurality of light emitting devices are mounted on opposite sides of said substrate.

33. The apparatus of claim 31, wherein the plurality of light emitting devices are mounted in a corresponding plurality of apertures formed in the substrate and emit light outwardly from both sides of the substrate.

34. The apparatus of claim 29, where, in said probe is enclosed within a structure that is:
(a) substantially optically transparent;
(b) thermally conductive;
(c) includes an optical diffuser; and (a) electrically insulating.

35. The apparatus of claim 34, wherein a material comprising the structure is selected for a characteristic heat transfer property that enables it to conduct waste heat generated by the light source that is disposed within the probe to the treatment site, application of said waste heat to the treatment site increasing an efficacy of the photodynamic treatment.

36. The apparatus of claim 20, wherein the power supply comprises a primary transformer winding coupled to a source of alternating current, and a secondary transformer winding that is adapted to be disposed entirely within the patient's body and which is electrically coupled to a rectifier, a direct current developed by said rectifier being electrically coupled to said light source, said primary transformer winding being adapted to inductively couple, transcutaneously, to the secondary transformer winding, an alternating electrical current inductively developed in the secondary transformer winding being rectified by the rectifier to produce the electrical current that is used to energize the light source disposed internally inside the patient's body.

37. The apparatus of claim 29, wherein the light source comprises at least one of a light emitting diode and a laser diode, further comprising means for monitoring a temperature of the probe as a function of an electrical current-voltage characteristic of said at least one of the light emitting diode and the laser diode.

38. The apparatus of claim 20, further comprising at least one reservoir for holding at least one fluid, and means for controllably perfusing said at least one fluid from said at least one reservoir into the treatment site.

39. The apparatus of claim 38, wherein said at least one reservoir is adapted to be disposed inside a patient's body.

40. The apparatus of claim 38, wherein the supporting structure comprises a multi-lumen catheter having a proximal end and a distal end, at least one of said lumens having an opening at the distal end of the catheter, each of said at least one lumens coupling to a different corresponding reservoir, which is disposed outside the patient's body, in fluid communication with the internal, in vivo treatment site to enable perfusion of fluid from each corresponding reservoir into said treatment site through the catheter.

41. The apparatus of claim 20, wherein the supporting structure is shaped to support a plurality of light emitting devices comprising the light source, in an array configured to provide a predefined pattern of illumination to the internal, in vivo treatment site.

42. The apparatus of claim 20, wherein the supporting structure and light source comprise materials selected to be physiologically inert so that the supporting structure and light source are adapted to be implanted in the patient's body for a time period over which the internal, in vivo treatment site is photodynamically treated.

43. The apparatus of claim 20, wherein the light source comprises a plurality of lasers arranged in an array, and the supporting structure comprises a panel on which the plurality of lasers are mounted, selected ones of said plurality of lasers being sequentially energized to provide light that irradiates different portions of the internal, in vivo treatment site.

44. The apparatus of claim 43, wherein each of the plurality of lasers is individually controllable to provide a predefined light pattern at the internal, in vivo treatment site.

45. The apparatus of claim 20, wherein the light source comprises at least one vertical cavity, surface emitting laser.

46. The apparatus of claim 20, wherein the light source includes means for diffusing the light over the internal, in vivo treatment site.

47. A method for photodynamic treatment at an internal, in vivo treatment site in a patient's body, to cause a desired therapeutic change, comprising the steps of:
(a) exposing the internal, in vivo treatment site, so that it is accessible from outside the patient's body;
(b) applying a photoreactive agent to the internal, in vivo treatment site, said photoreactive agent being selected for a characteristic wavelength or waveband of light absorption;
(c) transcutaneously implanting a light source proximate to the treatment site, said light source having an emission wavelength or waveband substantially equal to a wavelength or waveband of light absorption of the photoreactive agent;
(d) closing the light source inside the patient's body; and
(e) administering light to the treatment site from the light source, said light being absorbed by the photoreactive agent, which then causes the desired therapeutic change.

48. Apparatus for administering a photodynamic treatment at an internal, in vivo treatment site, to cause a desired therapeutic change, comprising:
(a) a light source having at least one emission wavelength or waveband substantially equal to a predefined light absorption wavelength or waveband required for the photodynamic treatment;
(b) a supporting structure for said light source, said supporting structure being adapted to be invasively transcutaneously implanted and left enclosed within a patient's body, proximate said internal, in vivo treatment site, and shaped to administer the light directly to the internal, in vivo treatment site, light emitted by the light source causing said desired therapeutic change; and
(c) a power supply that provides an electrical current to energize the light source without using conductors extending outside of the patient's body in which the light source is implanted.

49. A method for photodynamic treatment at an internal, in vivo treatment site in a patient's body, to cause a desired therapeutic change, comprising the steps of:
(a) applying a photoreactive agent to the internal, in vivo treatment site, said photoreactive agent being selected for at least one characteristic wavelength or waveband of light absorption;
(b) providing an array of individually addressable light emitting devices that are spaced apart from the internal, in vivo treatment site, said light emitting devices having at least one predefined emission wavelength or waveband as required for the photodynamic treatment; and
(c) administering light to the internal, in vivo treatment site from the array of light emitting devices by selectively energizing specific ones of the light emitting devices to achieve a desired pattern of light illuminating the treatment site, said light causing the desired therapeutic change.

50. The method of claim 49, wherein the step of administering light comprises the step of sequentially energizing a predefined number of the light emitting devices at a time, thereby multiplexing the light emitting devices.

51. The method of claim 49, further comprising the step of conveying light emitted by the light emitting devices to the internal, in vivo treatment site over a plurality of optical paths.

52. The method of claim 49, further comprising the step of modulating the light intensity emitted by at least selected light emitting devices in the array, to achieve a desired pattern of illumination of the internal, in vivo treatment site.

53. Apparatus for photodynamic treatment of an internal, in vivo treatment site to cause a desired therapeutic change, comprising:
  (a) an array of individually addressable light emitting devices that are spaced apart from the internal, in vivo treatment site, said light emitting devices each having at least one predefined emission wavelength or waveband required for the photodynamic treatment;
  (b) means for selectively energizing specific ones of the light emitting devices at a time to emit light that illuminates the internal, in vivo treatment site, to cause the desired therapeutic change; and
  (c) a power supply that is coupled to the means for selectively energizing, to supply electrical current to energize the specific ones of the light emitting devices in the array.

54. The apparatus of claim 53, wherein the means for selectively energizing include means for multiplexing the light emitting devices by only energizing a predefined number of the light emitting devices at a time.

55. The apparatus of claim 53, further comprising optical light paths that convey light from the light emitting devices comprising the array, to the internal, in vivo treatment site.

56. The apparatus of claim 55, wherein the light paths comprise optical fibers that extend between the light emitting devices and the internal, in vivo treatment site.

57. The apparatus of claim 54, wherein the means for selectively energizing include means for modulating the light intensity of the light emitting devices to produce a desired pattern of illumination on the internal, in vivo treatment site.

58. A method for photodynamic treatment at a treatment site in a patient's head, said treatment site including at least one of a sinus cavity, a nasal pharyngeal surface, a mouth surface, a throat surface, and an inner aural surface, to cause a desired therapeutic change, comprising the steps of:
  (a) applying a photoreactive agent to the treatment site inside the patient's head, said photoreactive agent being selected for at least one characteristic wavelength or waveband of light absorption;
  (b) positioning a light source proximate to the treatment site to illuminate the treatment site both internally and externally of the patient's head, said light source having at least one emission wavelength or waveband substantially equal to a wavelength or waveband of absorption of the photoreactive agent; and
  (c) administering light to the treatment site from the light source, said light being absorbed by the photoreactive agent, which then causes the desired therapeutic change.

59. A method for photodynamic treatment at an internal, in vivo treatment site, to cause a desired therapeutic change, comprising the steps of:
  (a) applying a photoreactive agent to the internal, in vivo treatment site, said photoreactive agent being selected for one or more characteristic wavelengths or wavebands of light absorption;
  (b) positioning a light source internally within a patient's body, said light source being transcutaneously delivered to and implanted at the in vivo treatment site, said light source emitting a light having one or more emission wavelengths or wavebands substantially equal to a wavelength or waveband of absorption of the photoreactive agent;
  (c) electromagnetically coupling power from an external power source to the light source to energize the light source during the photo dynamic treatment without directly connecting the external power source to the light source via a conductor; and
  (d) administering light emitted flora the light source to the internal, in vivo treatment site, said light being absorbed by the photoreactive agent, which then causes the desired therapeutic change at the treatment site.

60. The method of claim 59, wherein the step of electromagnetically coupling comprises the steps of:
  (a) energizing a transmitter that is external to the patient's body with a radio frequency signal produced by the external power source;
  (b) positioning the transmitter adjacent a receiver that is internal to the patient's body and coupled to the light source; and
  (c) transmitting the radio frequency signal from the transmitter to the receiver to produce an electrical current in the receiver, said electrical current in the receiver being used to energize the light source.

61. Apparatus for administering photo dynamic treatment at an internal, in vivo treatment site, to cause a desired therapeutic change, comprising:
  (a) a light source having at least one characteristic emission wavelength or waveband suitable for the photodynamic treatment;
  (b) a supporting structure for said light source, said supporting structure being adapted for invasive disposition within a patient's body, to support the light source proximate to said internal, in vivo treatment site, shaped to administer light directly to said treatment site from the light source, and adapted to be inserted transcutaneously and left in place during the photodynamic treatment, allowing said light source to be selectively energized to irradiate the internal, in vivo treatment site with said light, to cause the desired therapeutic change at the treatment site;
  (c) an external power source for supplying an electrical current to a transmitter that is adapted to be positioned externally adjacent a patient's body, proximate the treatment site; and
  (d) a receiver that is adapted to be implanted within the patient's body and coupled to the light source disposed at the treatment site, said transmitter electromagnetically coupling the electrical current produced by the external power source to the receiver, to induce an electrical current to flow in the receiver for energizing the light source.

* * * * *

UNITED STATES PATENT AND TRADEMARK OFFICE
CERTIFICATE OF CORRECTION

PATENT NO. : 5,445,608
DATED : August 29, 1995
INVENTOR(S) : James C. Chen et al.

It is certified that error appears in the above-indentified patent and that said Letters Patent is hereby corrected as shown below:

On the title page, first two corrections.

| | |
|---|---|
| Item [56] Other Publications, 9th Reference | "Haas" should read --Hass-- |
| Item [56], Other Publications, 14th Reference | "Systematic" should read --Systemic-- |
| Column 2, line 64 | ":similar" should read --similar-- |
| Column 6, line 6 | ":for" should read --for-- |
| Column 6, line 42 | "sources:;" should read --sources;-- |
| Column 9, line 15 | "more;" should read --more-- |
| Column 10, line 14 | "art" should read --an-- |
| Column 10, line 30 | "44''" should read --44'-- |
| Column 11, line 14 | "2LED" should read --LED-- |
| Column 11, line 24 | ";are" should read --are-- |
| Column 12, line 31 | after "downwardly" insert --,-- (comma) |
| Column 12, line 68 and Column 13, line 1 | "multi-plexing;" should read --multiplexing-- |
| Column 14, line 2 | "riot" should read --not-- |
| Column 14, line 25 | "genetic" should read --generic-- |

UNITED STATES PATENT AND TRADEMARK OFFICE
CERTIFICATE OF CORRECTION

PATENT NO. : 5,445,608
DATED : August 29, 1995
INVENTOR(S) : James C. Chen et al.

It is certified that error appears in the above-indentified patent and that said Letters Patent is hereby corrected as shown below:

| | |
|---|---|
| Column 15, line 43 | ";protocol," should read --protocol, |
| Column 17, line 26 | "of the 0P" (number zero) should read --of the OP-- (letter O) |
| Column 18, line 32 | "bastrointestinal" should read --gastrointestinal-- |
| Column 19, line 50 | "not" should read --*not*-- |
| Column 20, line 33 | "surface,'" should read --surface-- |
| Column 20, line 52 | "fibs" should read --ribs-- |
| Column 21, line 5 | "fibs" should read --ribs-- |
| Column 22, line 15 | "planiar" should read --planar-- |
| Column 24, line 50 | "coveting" should read --covering-- |
| Column 24, line 55 | "nostrils" should read --nostril's-- |
| Column 26, line 21, Claim 5, line 2 | "source, comprises" should read --source comprises-- |
| Column 29, line 1, Claim 34, line 6 | "(a)" should read --(d)-- |
| Column 31, line 41, Claim 57, line 1 | "Claim 54" should read --Claim 53-- |
| Column 32, line 17, Claim 59, line 17 | "photo dynamic" should read --photodynamic-- |

UNITED STATES PATENT AND TRADEMARK OFFICE
CERTIFICATE OF CORRECTION

PATENT NO. : 5,445,608

DATED : August 29, 1995

INVENTOR(S) : James C. Chen et al.

It is certified that error appears in the above-indentified patent and that said Letters Patent is hereby corrected as shown below:

Column 32, line 17,　　　"flora" should read --from--
Claim 59, line 21

Column 32, line 38,　　　"photo dynamic" should read --photodynamic--
Claim 61, line 1

Signed and Sealed this

Nineteenth Day of March, 1996

Attest:

BRUCE LEHMAN

*Attesting Officer*　　　　*Commissioner of Patents and Trademarks*